(12) United States Patent
Chan et al.

(10) Patent No.: US 8,921,571 B2
(45) Date of Patent: Dec. 30, 2014

(54) PYRROLYSINE ANALOGS

(75) Inventors: Michael K. Chan, Hilliard, OH (US); Tomasz Fekner, Lublin (PL); Xin Li, Albany, CA (US); Marianne Lee, Hilliard, OH (US); Manoj Nair, Columbus, OH (US); Jennifer Jo Ottensen, Worthington, OH (US)

(73) Assignee: The Ohio State University, Columbus, OH (US)

( * ) Notice: Subject to any disclaimer, the term of this patent is extended or adjusted under 35 U.S.C. 154(b) by 333 days.

(21) Appl. No.: 13/500,695

(22) PCT Filed: Oct. 6, 2010

(86) PCT No.: PCT/US2010/051658
§ 371 (c)(1),
(2), (4) Date: Oct. 24, 2012

(87) PCT Pub. No.: WO2011/044255
PCT Pub. Date: Apr. 14, 2011

(65) Prior Publication Data
US 2013/0035478 A1    Feb. 7, 2013

Related U.S. Application Data

(60) Provisional application No. 61/249,084, filed on Oct. 6, 2009.

(51) Int. Cl.
*C07D 277/06* (2006.01)
*C07D 229/02* (2006.01)
*C07C 53/124* (2006.01)
*C07C 233/47* (2006.01)
*C07C 247/04* (2006.01)
*C07C 247/12* (2006.01)
*C07C 229/28* (2006.01)
*C07C 323/60* (2006.01)
*C07C 237/16* (2006.01)
*C07C 323/25* (2006.01)

(52) U.S. Cl.
CPC ............ *C07D 277/06* (2013.01); *C07C 247/12* (2013.01); *C07C 229/28* (2013.01); *C07D 229/02* (2013.01); *C07C 323/60* (2013.01); *C07C 237/16* (2013.01); *C07C 323/25* (2013.01)
USPC ................ 548/200; 548/960; 562/507; 552/1

(58) Field of Classification Search
None
See application file for complete search history.

(56) References Cited

U.S. PATENT DOCUMENTS

2006/0183888 A1    8/2006    Chan et al.
2009/0111147 A1    4/2009    Miao et al.

OTHER PUBLICATIONS

Nguyen et al., "Genetic Encoding and Labeling of Aliphatic Azides and Alkynes in Recombinant Proteins via a Pyrrolysyl-tRNA Synthetase/RNACUA Pair and Click Chemistry", JACS, Jun. 10, 2009, vol. 131, pp. 8720-8721, p. 8720, Fig. 1A.
International Preliminary Report on Patentability issued Apr. 11, 2012 for International application No. PCT/US2010/051658.

*Primary Examiner* — Michael Barker
(74) *Attorney, Agent, or Firm* — Fay Sharpe LLP

(57) ABSTRACT

Several different pyrrolysine analogs are disclosed in this application. Those analogs have distinct chemical and biophysical properties. Some analogs are useful in chemical ligation applications. Methods of making and using are also disclosed.

19 Claims, 15 Drawing Sheets

PYRROLYSINE ANALOGS

This application claims priority to U.S. Provisional Patent Application Ser. No. 61/249,084, filed Oct. 6, 2009. The entire disclosure of that application is hereby fully incorporated by reference herein.

BACKGROUND

The present disclosure relates to pyrrolysine analogs.

Pyrrolysine is the 22nd genetically encoded amino acid. Pyrrolysine (Pyl) is encoded using a UAG codon (i.e. the amber stop codon), wherein rather than terminating the protein, Pyl is inserted instead. This phenomenon of transcription beyond the stop codon is known as readthrough. A pyrrolysyl-tRNA synthetase specifically charges a tRNA$^{Pyl}$ with pyrrolysine, which can then be incorporated into a protein.

Pyrrolysine contains a methyl-substituted 1-pyrroline group having an imine nitrogen. Pyrrolysine has the structure shown below:

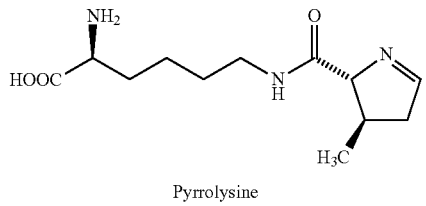

Pyrrolysine

BRIEF DESCRIPTION

The present disclosure relates to various pyrrolysine analogs. Those analogs are useful in different applications. Methods of making the analogs, methods of using the analogs, and other applications are also described herein.

These and other non-limiting characteristics of the disclosure are more particularly disclosed below.

BRIEF DESCRIPTION OF THE FIGURES

The following is a brief description of the figures, which are presented for the purposes of illustrating the exemplary embodiments disclosed herein and not for the purposes of limiting the same.

DETAILED DESCRIPTION

Figure 1:
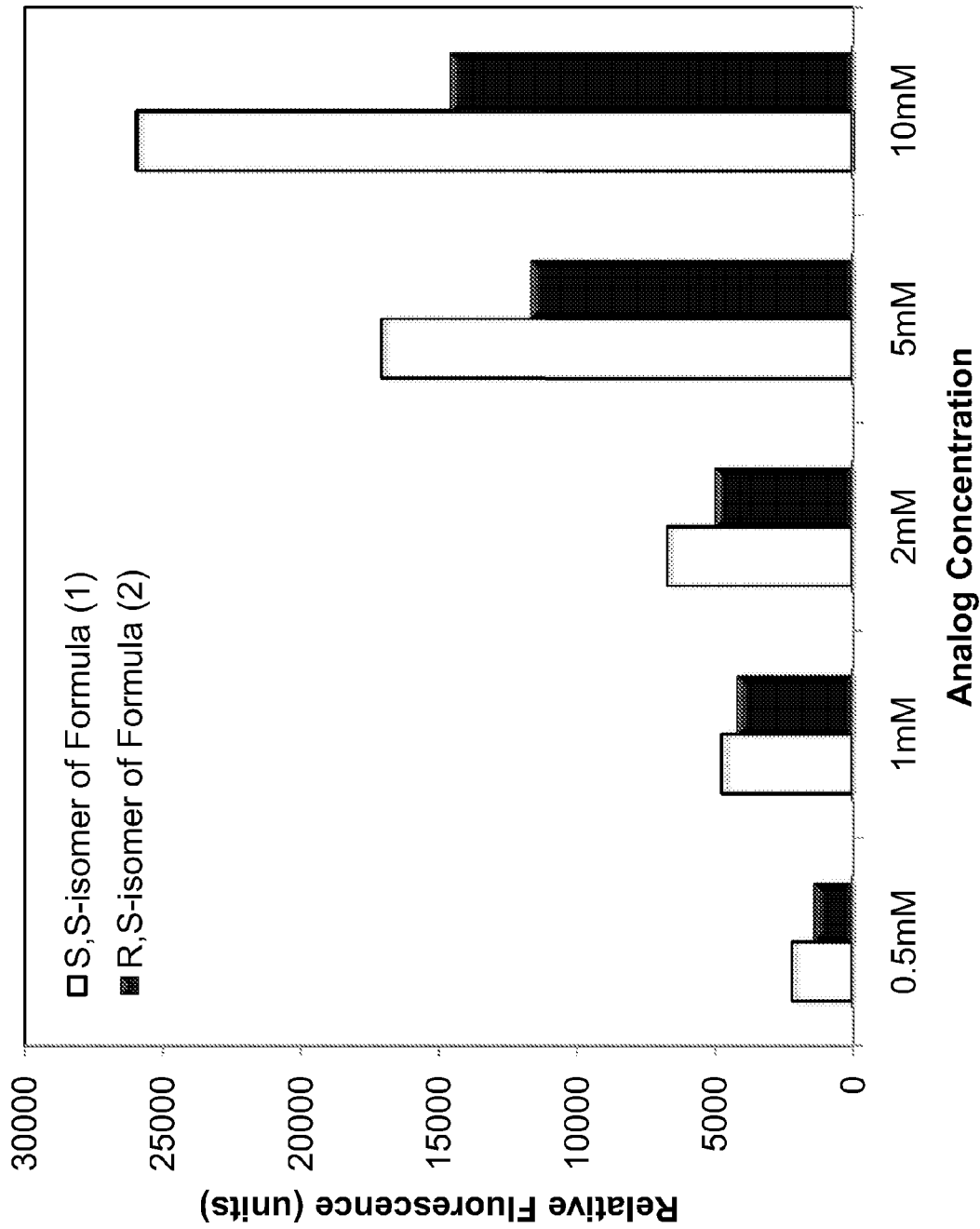
FIG. 1 is a graph comparing the readthrough efficiency of two isomers of a pyrrolysine analog as described herein.

A more complete understanding of the compositions, methods, and applications disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The term "ester" refers to a —COO— linkage. The term "thioester" refers to a —(C=O)—S— linkage. The term "carbonyl" refers to a —CO— linkage.

The term "ether" refers to —C—O—C— linkage. The term "thioether" refers to a —C—S—C— linkage.

The term "carbamate" refers to —O—(C=O)—NH— linkage. The term "amide" refers to a —(C=O)—NH— linkage.

The term "cystyl" refers to the radical —CH(—NH$_2$)CH$_2$SH. The term "isocystyl" refers to the radical —CH(—SH)CH$_2$(—NH$_2$).

The term "alkyl" is used in two different contexts herein, first as a linkage and second as a substituent or sidechain. When present as a substituent or sidechain, the term "alkyl" refers to a univalent radical composed entirely of carbon atoms and hydrogen atoms which is fully saturated and of the formula C$_n$H$_{2n+1}$. A substituent alkyl group may be considered an alkane with one hydrogen atom removed. Exemplary substituent alkyl groups include methyl (—CH$_3$), n-butyl (—CH$_2$CH$_2$CH$_2$CH$_3$), and t-butyl (—C—(CH$_3$)$_3$). When present as a linkage, the term "alkyl" or "alkylene" refers to a divalent radical composed entirely of carbon atoms and hydrogen atoms which is fully saturated and of the formula C$_n$H$_{2n}$. An exemplary linking alkyl group is methylene (—CH$_2$—). In either context, an alkyl group may be linear or branched.

The term "cycloalkyl" is used in two different contexts herein, first as a linkage and second as a substituent or sidechain. When present as a substituent or sidechain, the term "cycloalkyl" refers to a univalent radical composed entirely of carbon atoms and hydrogen atoms which is not aromatic (i.e. can be saturated or unsaturated) and has a ring structure. Exemplary cycloalkyl groups include cyclohexyl ($-C_6H_{11}$) and cyclohexenyl ($-C_6H_9$). When present as a linkage, the term "cycloalkyl" or "cycloalkylene" refers to a divalent radical composed entirely of carbon atoms and hydrogen atoms which is not aromatic and has a ring structure, such as cyclohexylene ($-C_6H_{10}-$).

The term "alkoxy" refers to a univalent alkyl radical which is subsequently attached to an oxygen atom at one end. An exemplary alkoxy group is methoxy ($-OCH_3$).

The term "alkynyl" refers to a radical composed entirely of carbon atoms and hydrogen atoms which contains one or more carbon-carbon triple bonds.

The term "aryl" refers to an aromatic radical composed entirely of carbon atoms and hydrogen atoms. Exemplary aryl groups include phenyl ($-C_6H_5$) and naphthyl ($-C_{10}H_7$).

The term "heterocyclic" refers to a radical which is originally composed of carbon atoms and hydrogen atoms, has a ring structure, and can be saturated or unsaturated. One or more of the carbon atoms is then replaced by a heteroatom, generally nitrogen, oxygen, or sulfur, to obtain a heterocyclic group. Exemplary heterocyclic groups include furanyl ($-C_4H_3O$), dioxolanyl ($-C_3H_5O_2$), pyrrolidinyl ($-C_4H_8N$), pyrrolyl ($C_4H_4N$), and thienyl ($-C_4H_3S$). The term "heteroaryl" refers generally to a heterocyclic aromatic radical, and may be considered a subset of heteroatom-containing groups. The heterocyclic radical may be univalent or divalent, depending on whether it is used as a linkage or as a substituent/sidechain.

The term "halogen" refers to fluorine, chlorine, bromine, and iodine atoms. The term "amino" refers to a $-NH_2$ radical.

The term "peptide" refers to the polymer formed by the linking of two or more amino acids. In common usage, a peptide is a short chain, while a "polypeptide" or protein is a long chain. Any specific numerical distinction between a peptide, oligopeptide, and polypeptide is arbitrary. As used herein, these terms are used to denote relative lengths, and should not be construed as requiring a certain number of amino acids to be linked together to fall within one group but not another.

Several different pyrrolysine analogs are disclosed in this application. These pyrrolysine analogs can be incorporated into a recombinant protein. This allows the analogs to be involved in many different reaction types including but not limited to native chemical ligation, click chemistry, and traceless Staudinger ligation reactions. These reactions can be useful in applications such as site-specific ubiquitination, SUMOylation, tagging of biological materials with fluorescent dyes or other dyes or affinity tags, generation of thermostable proteins, generation of cyclic peptides, phoactivatible crosslinking, Forster (or fluorescence) resonance energy transfer, and site-specific biotinylation.

Some pyrrolysine analogs have the structure of Formula (I):

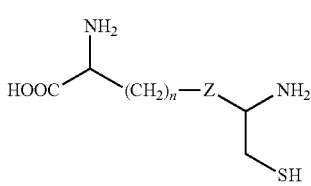

Formula (I)

wherein n is from 0 to 8; and Z is a linkage selected from the group consisting of ester, thioester, carbonyl, ether, thioether, carbamate, and amide. In some embodiments of Formula (I), n is 4. In other embodiments, Z is amide, ester, or carbonyl.

Some pyrrolysine analogs have the structure of Formula (II):

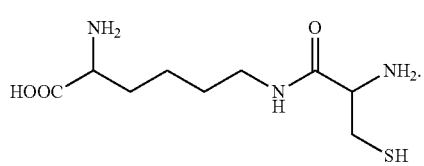

Formula (II)

Additional pyrrolysine analogs have the structure of Formula (III):

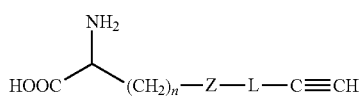

Formula (III)

wherein n is from 0 to 8;
Z is a linkage selected from the group consisting of ester, thioester, carbonyl, ether, thioether, carbamate, and amide; and
L is a linkage selected from the group consisting of alkyl and cycloalkyl, either of which may be substituted with one or more substituents selected from the group consisting of alkoxy, halogen, hydroxyl, amino, and thiol.

In some embodiments of Formula (III), n is 4. In other embodiments, Z is amide or ester. In other embodiments, L is alkyl or substituted alkyl.

Further pyrrolysine analogs have the structure of Formula (IV):

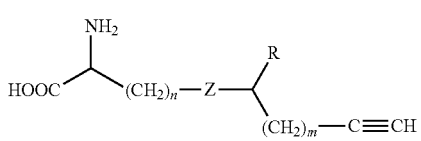

Formula (IV)

wherein n is from 0 to 8;
Z is a linkage selected from the group consisting of ester, thioester, carbonyl, ether, thioether, carbamate, and amide;
m is from 1 to 6; and
R is selected from the group consisting of alkoxy, halogen, hydroxyl, amino, and thiol.

In particular embodiments of Formula (IV), n is 4. In other embodiments, Z is amide or ester. In some embodiments, m is 1. In specific embodiments, n is 4; m is 1; and Z is amide or ester.

Additional pyrrolysine analogs have the structure of Formula (IV-a):

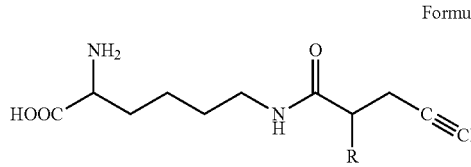

Formula (IV-a)

wherein R is selected from the group consisting of alkoxy, halogen, hydroxyl, amino, and thiol.

Still further pyrrolysine analogs have the structure of Formula (V):

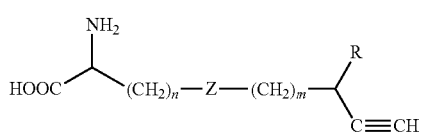

Formula (V)

wherein n is from 0 to 8;
Z is a linkage selected from the group consisting of ester, thioester, carbonyl, ether, thioether, carbamate, and amide;
m is from 1 to 6; and
R is selected from the group consisting of alkoxy, halogen, hydroxyl, amino, and thiol.

In particular embodiments of Formula (V), n is 4. In other embodiments, Z is amide or ester. In some embodiments, m is 1. In specific embodiments, n is 4; m is 1; and Z is amide or ester.

Other pyrrolysine analogs have the structure of Formula (VI):

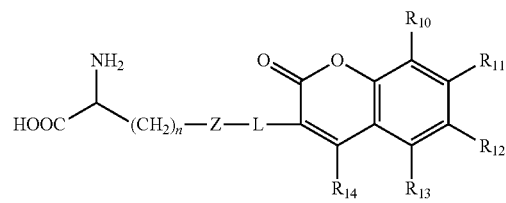

Formula (VI)

wherein n is from 0 to 8;
Z is a linkage selected from the group consisting of ester, thioester, carbonyl, ether, thioether, carbamate, and amide;
L is a linkage selected from the group consisting of alkyl, cycloalkyl, and heterocyclic, any of which may be substituted with one or more substituents selected from the group consisting of alkoxy, halogen, hydroxyl, amino, and thiol; and
$R_{10}$, $R_{11}$, $R_{12}$, $R_{13}$, and $R_{14}$ are independently selected from the group consisting of hydrogen, alkyl, alkoxy, halogen, hydroxyl, amino, and thiol.

In particular embodiments of Formula (VI), n is 4. In other embodiments, Z is amide or ester. In some embodiments, L is alkyl, particularly —CH$_2$—. In others, $R_{11}$ is alkoxy.

Still additional pyrrolysine analogs have the structure of Formula (VII):

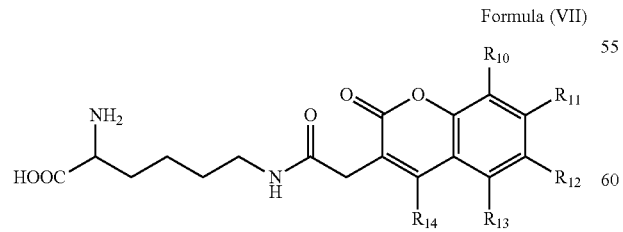

Formula (VII)

wherein $R_{10}$, $R_{11}$, $R_{12}$, $R_{13}$, and $R_{14}$ are independently selected from the group consisting of hydrogen, alkyl, alkoxy, halogen, hydroxyl, amino, and thiol. In specific embodiments, $R_{11}$ is alkoxy.

Some pyrrolysine analogs have the structure of Formula (VIII):

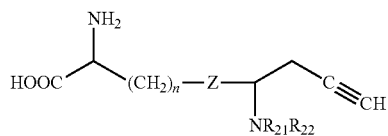

Formula (VIII)

wherein n is from 0 to 8;
Z is a linkage selected from the group consisting of ester, thioester, carbonyl, ether, thioether, carbamate, and amide; and
either (i) $R_{21}$ and $R_{22}$ are independently selected from the group consisting of hydrogen, alkyl, substituted alkyl, cycloalkyl, substituted cycloalkyl, aryl, substituted aryl, heterocyclic, substituted heterocyclic, alkoxy, and halogen; or (ii) $NR_{21}R_{22}$ denotes a nitrogen-containing heterocyclic group.

In particular embodiments of Formula (VIII), n is 4. In other embodiments, Z is amide or ester.

Further pyrrolysine analogs have the structure of Formula (IX):

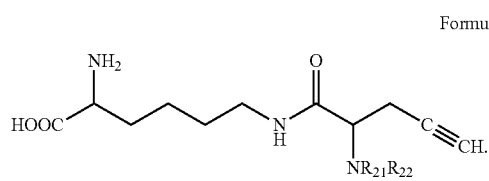

Formula (IX)

Other pyrrolysine analogs have the structure of Formula (X):

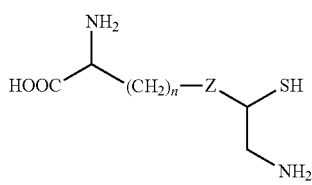

Formula (X)

wherein n is from 0 to 8; and Z is a linkage selected from the group consisting of ester, thioester, carbonyl, ether, thioether, carbamate, and amide.

In particular embodiments of Formula (X), n is 4. In other embodiments, Z is amide or ester.

Additional pyrrolysine analogs have the structure of Formula (XI):

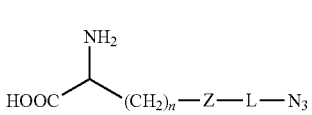

Formula (XI)

wherein n is from 0 to 8;
Z is a linkage selected from the group consisting of ester, thioester, carbonyl, ether, thioether, and amide; and
L is a linkage selected from the group consisting of alkyl, cycloalkyl, and heterocyclic, any of which may be substituted with one or more substituents selected from the group consisting of alkoxy, halogen, hydroxyl, amino, and thiol.

In particular embodiments of Formula (XI), n is 4. In other embodiments, Z is amide or ester. In some embodiments, L is alkyl, particularly —CH$_2$—.

Some pyrrolysine analogs have the structure of Formula (XII):

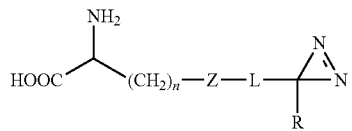

Formula (XII)

wherein n is from 0 to 8;

Z is a linkage selected from the group consisting of ester, thioester, carbonyl, ether, thioether, and amide;

L is a linkage selected from the group consisting of alkyl, cycloalkyl, and heterocyclic, any of which may substituted with one or more substituents selected from the group consisting of alkoxy, halogen, hydroxyl, amino, and thiol; and R is independently selected from the group consisting of hydrogen, alkyl, alkoxy, halogen, hydroxyl, amino, and thiol.

In particular embodiments of Formula (XII), n is 4. In other embodiments, Z is amide or ester. In some embodiments, L is alkyl, particularly —CH$_2$—. In others, R is —CH$_3$.

Other pyrrolysine analogs have the structure of Formula (XIII):

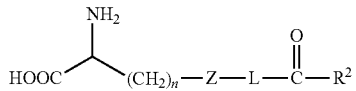

Formula (XIII)

wherein n is from 0 to 8;

Z is a linkage selected from the group consisting of ester, thioester, carbonyl, ether, thioether, and amide;

L is a linkage selected from the group consisting of alkyl, cycloalkyl, and heterocyclic, any of which may substituted with one or more substituents selected from the group consisting of alkoxy, halogen, hydroxyl, amino, and thiol; and R$^2$ is selected from the group consisting of hydrogen, alkyl, alkoxy, halogen, hydroxyl, amino, and thiol.

In particular embodiments of Formula (XIII), n is 4. In other embodiments, Z is amide or ester. In some embodiments, L is alkyl. In others, R$^2$ is hydrogen or alkyl.

Further pyrrolysine analogs have the structure of Formula (XIV):

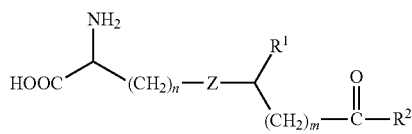

Formula (XIV)

wherein n and m are independently from 0 to 8;

Z is a linkage selected from the group consisting of ester, thioester, carbonyl, ether, thioether, and amide;

R$^1$ is hydrogen or amino; and

R$^2$ is selected from the group consisting of hydrogen, alkyl, alkoxy, halogen, hydroxyl, amino, and thiol.

In particular embodiments of Formula (XIV), n is 4. In other embodiments, Z is amide or ester. In some embodiments, R$^2$ is hydrogen or alkyl.

Still further pyrrolysine analogs have the structure of Formula (XV):

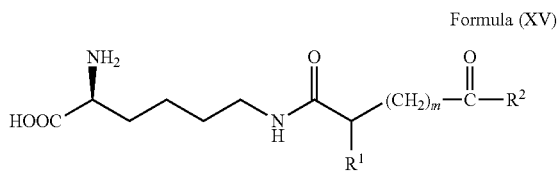

Formula (XV)

wherein m is from 0 to 8; R$^1$ is hydrogen or amino; and R$^2$ is hydrogen or alkyl.

Additional pyrrolysine analogs have the structure of Formula (XVI):

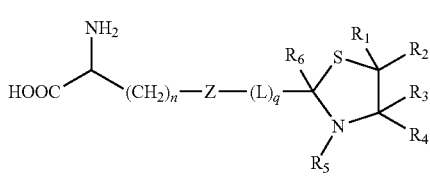

Formula (XVI)

wherein n is from 0 to 8;

Z is a linkage selected from the group consisting of ester, thioester, carbonyl, ether, thioether, and amide;

L is a linkage selected from the group consisting of alkyl, cycloalkyl, and heterocyclic, any of which may substituted with one or more substituents selected from the group consisting of alkoxy, halogen, hydroxyl, amino, and thiol;

q is 0 or 1; and

R$_1$, R$_2$, R$_3$, R$_4$, R$_5$, and R$_6$ are independently selected from the group consisting of hydrogen, alkyl, alkoxy, halogen, hydroxyl, amino, and thiol.

In particular embodiments of Formula (XVI), n is 4. In other embodiments, Z is amide or ester. In some embodiments, q is 0. In others, R$_1$, R$_2$, R$_3$, R$_4$, R$_5$, and R$_6$ are all hydrogen.

Some pyrrolysine analogs have the structure of Formula (XVII):

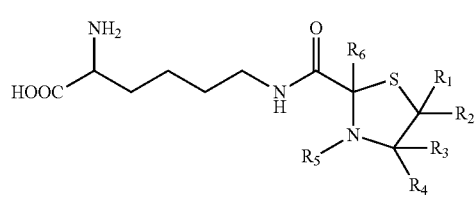

Formula (XVII)

wherein R$_1$, R$_2$, R$_3$, R$_4$, R$_5$, and R$_6$ are independently selected from the group consisting of hydrogen, alkyl, alkoxy, halogen, hydroxyl, amino, and thiol.

Other pyrrolysine analogs have the structure of Formula (XVIII):

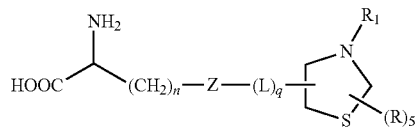

Formula (XVIII)

wherein n is from 0 to 8;
Z is a linkage selected from the group consisting of ester, thioester, carbonyl, ether, thioether, and amide;
L is a linkage selected from the group consisting of alkyl, cycloalkyl, and heterocyclic, any of which may substituted with one or more substituents selected from the group consisting of alkoxy, halogen, hydroxyl, amino, and thiol;
q is 0 or 1; and
$R_1$ and each R are independently selected from the group consisting of hydrogen, alkyl, alkoxy, halogen, hydroxyl, amino, and thiol.

In particular embodiments of Formula (XVIII), n is 4. In other embodiments, Z is amide or ester. In some embodiments, q is 0. In others, $R_1$ and all five R substituents are hydrogen.

Still further pyrrolysine analogs have the structure of Formula (XIX):

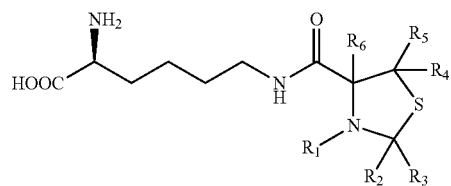

Formula (XIX)

wherein $R_1$, $R_2$, $R_3$, $R_4$, $R_5$, and $R_6$ are independently selected from the group consisting of hydrogen, alkyl, alkoxy, halogen, hydroxyl, amino, and thiol.

Specific pyrrolysine analogs disclosed herein include those having the structures of Formulas (1) through (19) and full chemical names as listed:

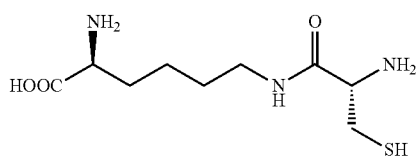

Formula (1)

(S,S)-2-amino-6-(2-amino-3-thiopropamido)-hexanoic acid

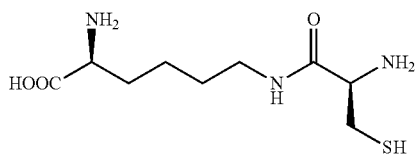

Formula (2)

(R,S)-2-amino-6-(2-amino-3-thiopropamido)-hexanoic acid

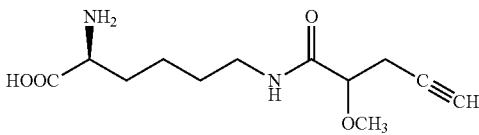

Formula (4)

(S)-6-(2-methoxypent-4-ynamido)-2-aminohexanoic acid

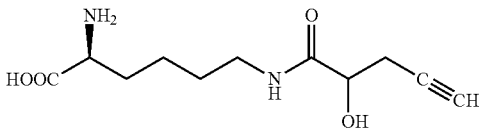

Formula (5)

(S)-6-(2-hydroxypent-4-ynamido)-2-aminohexanoic acid

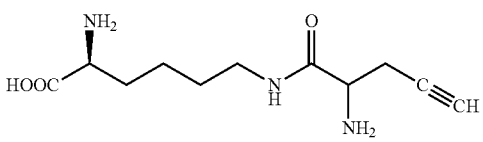

Formula (6)

(S)-6-(2-aminopent-4-ynamido)-2-aminohexanoic acid

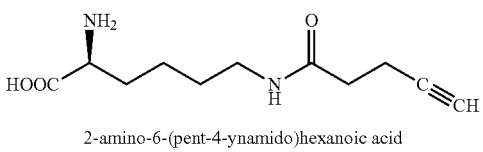

Formula (7)

2-amino-6-(pent-4-ynamido)hexanoic acid

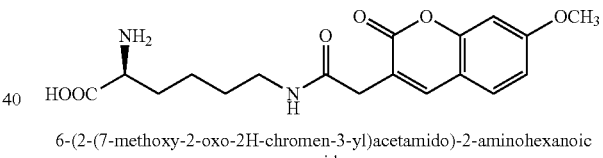

Formula (8)

6-(2-(7-methoxy-2-oxo-2H-chromen-3-yl)acetamido)-2-aminohexanoic acid

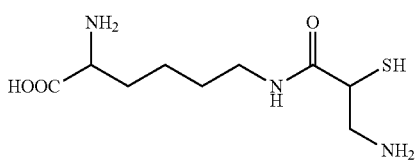

Formula (9)

2-amino-6-(2-thio-3-aminopropamido)-hexanoic acid

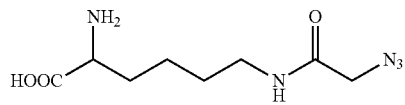

Formula (10)

2-amino-6-(azidoacetyl)-hexanoic acid

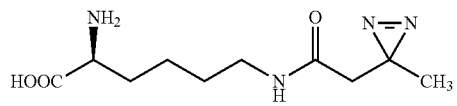

Formula (11)

6-(2-(3-methyl-3H-diazirin-3-yl)acetamido)-2-aminohexanoic acid

Formula (12)

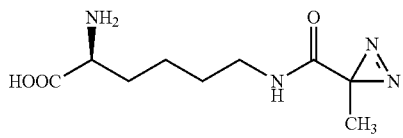

6-(3-methyl-3H-diazirine-3-carboxamido)-2-aminohexanoic acid

Formula (13)

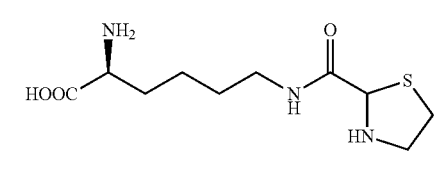

(S)-6-(2-carbamoylacetyl)-2-aminohexanoic acid

Formula (14)

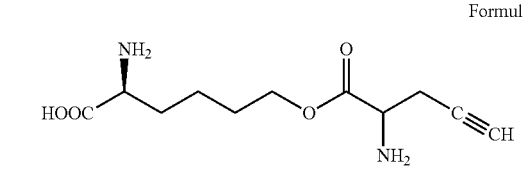

6-(thiazolidine-2-carboxamido)-2-aminohexanoic acid

Formula (15)

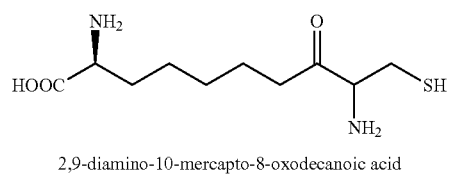

2-amino-6-(2-amino-4-pentynoyloxy)hexanoic acid

Formula (16)

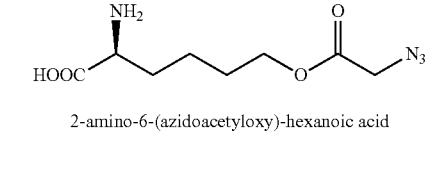

2,9-diamino-10-mercapto-8-oxodecanoic acid

Formula (17)

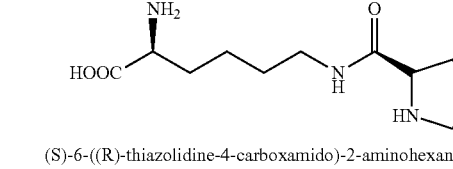

2-amino-6-(azidoacetyloxy)-hexanoic acid

Formula (18)

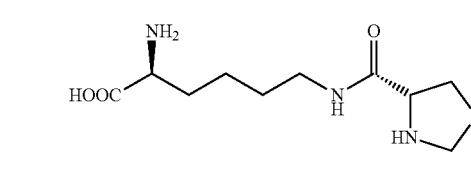

(S)-6-((R)-thiazolidine-4-carboxamido)-2-aminohexanoic acid

Formula (19)

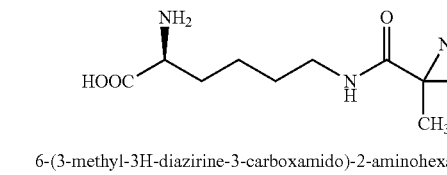

(S)-6-((S)-thiazolidine-4-carboxamido)-2-aminohexanoic acid.

Other variations of these pyrrolysine analogs, such as their salts or having protecting groups on various functional groups, are contemplated as being within the scope of this disclosure. In addition, the various stereoisomers are contemplated separately, as well as racemic mixtures of these analogs. Some studies indicate that the chirality of the lysine acyl substituent influences incorporation efficiency.

The analogs of Formula (II) are a subset of the analogs of Formula (I). The analogs of Formulas (1) and (2) are exemplary species of Formulas (I) and (II). The analog of Formula (16) is an exemplary species of Formula (I). The analogs of Formulas (I) and (II) are related to those of Formula (X), as well. The analogs of Formula (I) may be referred to as cysteine analogs.

The analogs of Formula (IV) and Formula (V) are a subset of the analogs of Formula (III). The analogs of Formula (IV-a) are a subset of the analogs of Formula (IV). The analogs of Formulas (4) through (7) are exemplary species of Formulas (III), (IV), and (IV-a). The analog of Formula (15) is an exemplary species of Formulas (III) and (IV).

The analogs of Formula (VII) are a subset of the analogs of Formula (VI). The analog of Formula (8) is an exemplary species of Formulas (VI) and (VII).

The analogs of Formula (IX) are a subset of the analogs of Formula (VIII). The analog of Formula (6) is an exemplary species of Formulas (VIII) and (IX). The analog of Formula (15) is an exemplary species of Formulas (VIII).

The analog of Formula (9) is an exemplary species of Formula (X). The analogs of Formula (X0 may be referred to as isocysteine analogs.

The analogs of Formulas (10) and (17) are exemplary species of Formula (XI).

The analogs of Formulas (11) and (12) are exemplary species of Formula (XII).

The analogs of Formulas (XIV) and (XV) are a subset of the analogs of Formula (XIII). The analog of Formula (13) is an exemplary species of Formulas (XIII), (XIV), and (XV).

The analogs of Formula (XVII) are a subset of the analogs of Formula (XVI). The analog of Formula (14) is an exemplary species of Formulas (XVI) and (XVII).

The analogs of Formula (XIX) are a subset of the analogs of Formula (XVIII). The analogs of Formulas (14), (18), and (19) are exemplary species of Formulas (XVIII). The analogs of Formulas (18) and (19) are exemplary species of Formula (XIX).

The pyrrolysine analogs disclosed herein can be made using various methods. For example, the analogs of Formulas (I) and (II) can be made by coupling a protected lysine of Formula (A) with a carboxylic acid of Formula (B):

Formula (A)

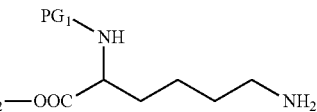

Formula (B)

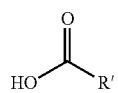

wherein $PG_1$ and $PG_2$ are independently a protecting group, and R' is a sidechain, to produce an amide. Any suitable protecting group can be used, such as triphenylmethyl (Trt), t-butoxycarbonyl (Boc), t-butyl (tBu), and t-butyldiphenylsilyl (TBDPS). The resulting amide is subsequently deprotected to obtain the pyrrolysine analog.

The structure of the carboxylic acid will vary depending on the desired analog. For example, the analog of Formula (II) can be obtained using the carboxylic acid of Formula (C); the analog of Formula (9) can be obtained using the carboxylic acid of Formula (D); and some analogs of Formula (IV) can be obtained using the carboxylic acid of Formula (E):

Formula (C)

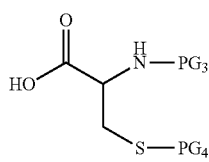

Formula (D)

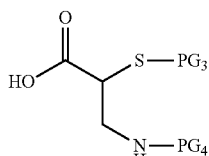

Formula (E)

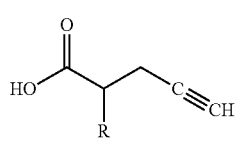

wherein PG$_3$ and PG$_4$ are independently protecting groups as described above, and R is a sidechain as described for Formula (IV).

The reaction conditions (time, temperature, pH, etc.) for the coupling and deprotecting reactions can generally be determined by one of ordinary skill in the art. The coupling of the protected lysine and the carboxylic acid can occur at a temperature of 0° C. to about 25° C., including room temperature (i.e. about 25° C.). The coupling reaction may occur for a period of 5 hours to 48 hours, including about 24 hours. The coupling reaction can also occur at a given pH, for example a pH of from about 8 to about 12. In particular embodiments, the coupling occurs in a solution of (benzotriazol-1-yloxy)tris(dimethylamino)phosphonium hexafluorophosphate, N-methylmorpholine, and dichloromethane.

The deprotecting of the protected amide can occur at a temperature of 0° C. to about 25° C., including room temperature (i.e. about 25° C.). The deprotecting reaction may occur for a period of about 1 hour to about 4 hours, including about 2 hours. The deprotecting reaction is typically carried out in neat trifluoroacetic acid (TFA), and the pH is determined by the pKa. In particular embodiments, the decoupling occurs in a solution of trifluoroacetic acid, triethylsilane, and dichloromethane.

As another example, pyrrolysine analogs 3 having an amide linkage (i.e. where Z is amide) can be formed by reacting a lysine residue 1 with a carboxylic acid 2, as shown below broadly in Scheme 1 (protecting groups not illustrated):

Scheme 1

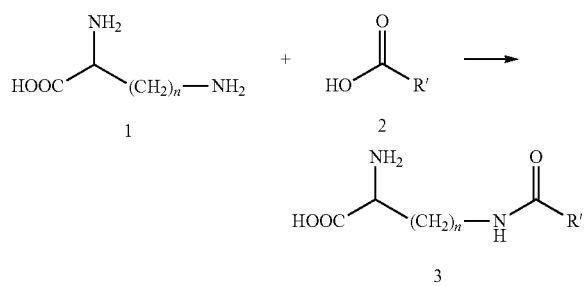

where R' is the relevant sidechain as described in Formulas (I)-(XII). For example, to form the analogs of Formulas (III), (IV), (V), and (VIII), the carboxylic acid would be a pent-4-ynoic acid.

Pyrrolysine analogs 5 having an ester or thioester linkage can be formed by reacting a lysine alcohol or thiol derivative 4 with a carboxylic acid 2, as shown below broadly in Scheme 2 (protecting groups not illustrated):

Scheme 2

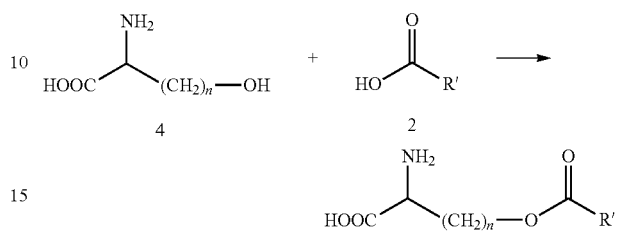

The analogs having carbonyl, ether, and carbamate linkages can also be made using similar methods known in the art, and are merely illustrated below:

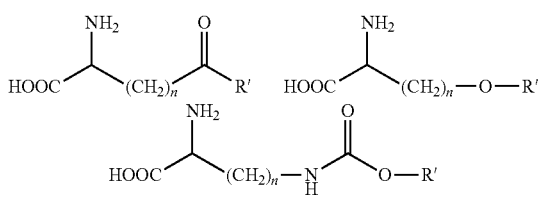

where R' is the relevant sidechain

The pyrrolysine analogs disclosed herein can be incorporated into a recombinant protein. This can be done by taking a nucleotide sequence that codes for the protein and mutating an original codon in that protein to a UAG codon. This allows for site-specific incorporation of the analog within a recombinant protein. Any codon for any amino acid can be changed to the amber codon, and the analog can then be incorporated at that site. It is recognized that incorporation at certain positions might disrupt the tertiary or quarternary structure of the protein. The mutated nucleotide sequence is then inserted into a vector and a cell is exposed to the vector, transforming the cell. If needed, the pyrrolysine tRNA gene and/or the pyrrolysine synthetase gene can also be provided to the cell, either in the same vector as the mutated nucleotide sequence or in different vectors. In some embodiments, the cell is also transformed to include a pyrrolysine tRNA gene (PylT) or a pyrrolysine synthetase gene (PylS). In particular embodiments, the nucleotide sequence, PylT, and PylS are inserted into the same vector. When the pyrrolysine analog is provided to the cell, the nucleotide sequence can be expressed to obtain the recombinant protein incorporating the pyrrolysine analog.

The pyrrolysine analogs disclosed herein are useful for many applications. One particular application is native chemical ligation (NCL), a strategy for the synthesis of large peptides or coupling of compounds having a thioester end with compounds having a cystyl or isocystyl group. Generally, a peptide having a C-terminal thioester is coupled with a peptide having an N-terminal cysteine to form a product having a native protein backbone. A reversible thioesterification in the presence of an exogenous thiol creates an intermediate which can undergo irreversible intramolecular S→N acyl transfer leading to a new peptide. Using a pyrrolysine analog places a ligation handle directly into a recombinant protein for use with NCL. In particular, the pyrrolysine analogs of Formulas (I) and (X) are useful for this purpose because their free end resembles cysteine. They may also be useful for non-native chemical ligation.

Disclosed are methods of creating a long polypeptide. A first peptide is made that incorporates a pyrrolysine analog of Formula (I) or (X) in the peptide. A second peptide is provided that has a thioester, for example on its C-terminal end. The "C-terminal end" refers to the end of the peptide having a free carboxylic acid group. The first peptide and the second peptide are then reacted to obtain or form the long polypeptide. As in NCL, the thioester reacts with the cysteine-like free end of the pyrrolysine analog of Formula (I) or (X) to join the two peptides. One advantage of using the pyrrolysine analog is that it can be incorporated at any position in the protein and the NCL reaction can then be carried out in a site-specific location. This allows a full-length recombinant protein to be coupled with another peptide in a site-specific location and provides freedom from the prior constraint of NCL allowing coupling only at the N-terminus end.

The molar ratio of the second peptide to the first peptide is generally greater than 1:1, and in embodiments can be about 5:1.

The first and second peptides can be reacted together in conditions (time, temperature, pH, etc.) which can generally be determined by one of ordinary skill in the art. For example, the reaction may occur within a temperature of about 4° C. to about 37° C., including room temperature (i.e. about 25° C.). The reaction may occur for a period of about 3 hours to about 3 days, including about 12 hours. The reaction can also occur at a given pH, for example from about 7.0 to about 8.0, including about pH 7.2.

Protein ubiquitination is a special post-translational modification in which the C-terminal glycine of the 76-residue protein ubiquitin is attached to the c-amino group of a lysine residue in a target protein via an isopeptide bond, and plays a role in many cellular processes. Replacing lysine residues in the target protein or in the ubiquitin protein itself with a pyrrolysine analog provides many opportunities for research into these cellular processes.

In some embodiments of the present methods, the C-terminal glycine of ubiquitin can be replaced with a D-cysteine residue and coupled to a pyrrolysine analog incorporated in a second protein via the native chemical ligation reaction. Alternatively, other proteins could be covalently coupled to the pyrrolysine analog incorporated in a second protein in a site-specific manner via the native chemical ligation reaction. In one embodiment, a small ubiquitin-like modifier (SUMO) protein is mutated to generate a thioester end and is thereafter coupled to a pyrrolysine analog incorporated in a second protein. In another embodiment, a first protein having a thioester end is coupled to a pyrrolysine analog in a second protein by the native chemical ligation reaction. In another embodiment, a first protein having a thioester end is coupled to a pyrrolysine analog of Formula (I) or (X) which has been incorporated into a second protein.

There are three types of ubiquitination: monoubiquitination, multiubiquitination, and polyubiquitination. Monoubiquitination is a single ubiquitin linking to a single lysine residue in the target protein. Multiubiquitination occurs when a ubiquitin protein links to multiple lysine residues in the target protein (1 ubiquitin protein per lysine residue). Polyubiquitination occurs when one or more ubiquitins link together to form a ubiquitin chain on a single lysine residue in the target protein (multiple ubiquitins linked to one lysine residue). Multiubiquitination and polyubiquitination may be present at the same time.

The 76-residue ubiquitin protein itself has seven lysine residues (K6, K11, K27, K29, K33, K48, K63). Polyubiquitins can be constructed in seven different linkages, depending on which of the seven lysine residues in the proximal ubiquitin is attacked by Gly76 of the distal ubiquitin. These different linkages have different topology, are recognized by different downstream proteins, and are decomposed by different deubiquinating enzymes. Thus, incorporating the pyrrolysine analogs to replace any of the seven lysine residues would provide additional information on many different cellular processes.

Small ubiquitin-like modifiers (SUMO) are a major class of proteins of small molecular weight (~8-20 kDa) that act like ubiquitin by altering protein properties through covalent attachment. Some members of this class (SUMO1, SUMO2, SUMO3) regulate a variety of functions in eukaryotic cells including DNA repair, transcription, nuclear transport and signal transduction in cells. Structures of SUMO1 modified target proteins have shown details of its intermolecular interaction with the target. One example is the structure of SUMO1 bound to thymidine DNA glycosylase (TDG) that induces a conformational change in the target protein antagonistic to DNA binding. The covalent ligation in vivo is mediated by a cascade of three ligases called E1, E2 and E3 resulting in an isopeptide linkage between the C-terminus of SUMO and the c-amino group of the lysine in the target. Again, incorporating pyrrolysine analogs into a target protein would provide information on many different cellular processes.

Thus, in some of the methods for creating a long polypeptide, the second peptide can be ubiquitin whose C-terminal glycine residue has been substituted with a D-cysteine residue and thioesterified. Alternatively, the second peptide is a small ubiquitin-like modifier. In other embodiments, the first peptide is ubiquitin, which has been modified so that the pyrrolysine analog replaces one of the seven lysine residues present in ubiquitin.

Another application is click chemistry. Fluorescent tagging of proteins allows the study of many processes. One challenging aspect is regiospecific incorporation of a fluorophore at a specific location in a protein. The pyrrolysine analogs of Formulas (III), (IV), (V), (VIII), and (IX) each contain a terminal alkyne group which enable site-specific post-translational modification of the protein into which they are incorporated with azide-based fluorophores via a $Cu^I$-catalyzed click reaction to form a triazole.

In particular, the D-isomer of the analog of Formula (6), shown below as Formula (6-a), has been found to be highly efficient in terms of readthrough efficiency.

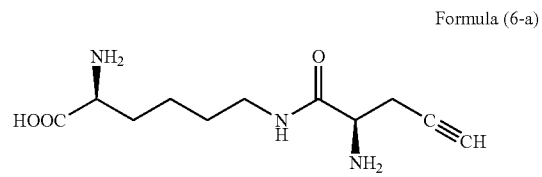 [SMILES: C#CC[C@@H](N)C(=O)NCCCC[C@H](N)C(=O)O]

Formula (6-a)

In other applications, it may be useful to label a protein with a fluorescent moiety, i.e. a fluorophore. Exemplary fluorophores include coumarin moieties, fluorescein moieties, and rhodamine moieties, and those moieties can be attached to the protein through the pyrrolysine analog. For example, the free end of the pyrrolysine analog can react with a probe containing a fluorophore. Alternatively, the probe may comprise a biotin derivative, such as $N_3$-biotin, so that biotinylation can be used. The protein can also be labeled with two fluorophores, which would be useful for Förster resonance energy transfer (FRET) experiments. The pyrrolysine analog is incorporated into the protein as previously described.

The pyrrolysine analogs of Formula (XI) each contain a terminal azide group which allow for corresponding site-specific post-translational modification of the protein into which they are incorporated with alkyne-based fluorophores via the Cu$^I$-catalyzed click reaction.

The analogs of Formula (XI) are also useful in traceless Staudinger ligation. Staudinger ligation is an aza-ylide forming reaction between an azide and a phosphine. A traceless Staudinger ligation forms a native amide bond between the reactants after removing the auxiliary phosphine reagent. The diagram below shows as an example how the structure of Formula (10) is incorporated into a target protein and is then linked to a thioester-containing 74-residue ubiquitin, labeled Ub(1-74). The ligation reaction is carried out in aqueous condition and forms an aza-ylide intermediate. The nucleophilic nitrogen atom of the aza-ylide will then attack the carbonyl group of Gly75 and cleave the thioester. The rearranged product is unstable and hydrolyzed to produce the peptide bond between Gly75 and Gly76. Since no cysteine is required for the ligation, this method will perfectly mimic a ubiquitination site on the target protein.

Formula (I) or (X) to form the cyclic peptide. One method of encoding such a peptide is described by Scott et al., *PNAS*, Nov. 23, 1999, vol. 96, no. 24, pp. 13638-13643, where the desired peptide sequence is spliced between two intein fragments that function as a heterodimeric intein, and a protein ligation excises the two intein fragments which religating the flanking domains into a contiguous peptide.

Cyclic peptides have been used as potential drugs and as recognition elements. In some embodiments, as depicted below, a protein (the rectangular box) could be generated that has a cyclic portion located at one end of a protein due to the placement of the pyrrolysine analog:

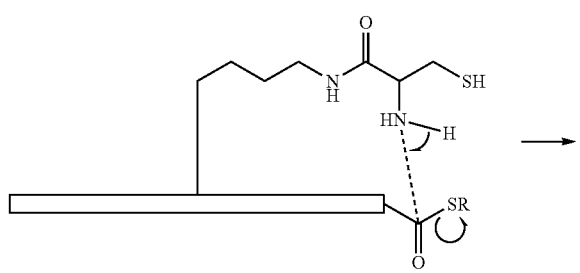

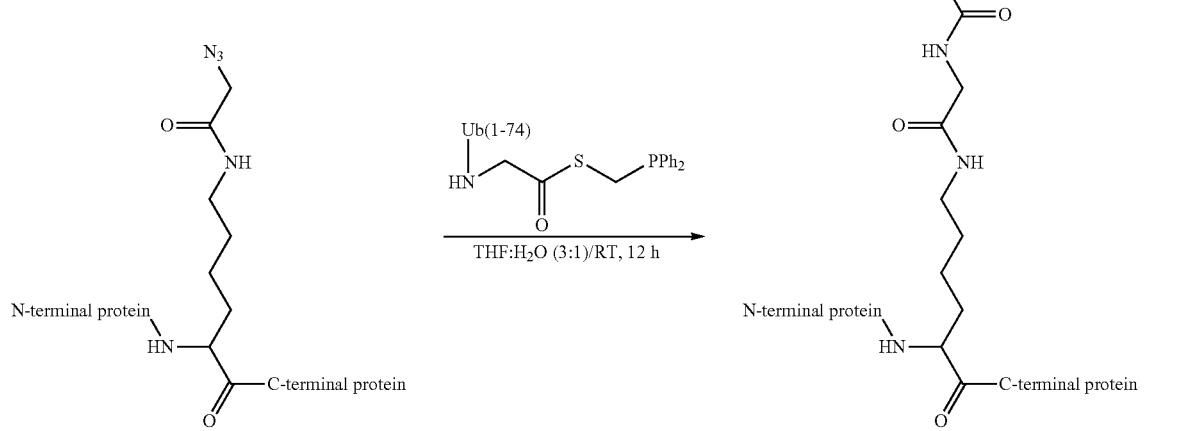

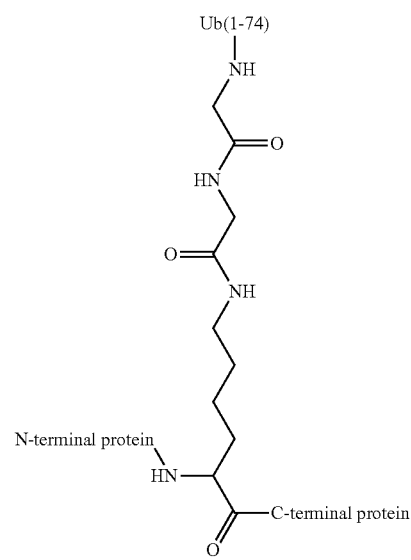

The analogs of Formula (XII) contain a diazirine moiety, which is stable but when photolyzed with ultraviolet (UV) light forms carbenes that can lead to permanent crosslinks. In other words, these pyrrolysine analogs can act as photoactivatable crosslinking agent. They may be used in site-specific labeling of proteins to aid in the identification of protein-protein interactions, the mechanisms of regulation of different biological pathways, and the functional role of proteins.

The pyrrolysine analogs of Formulas (I) or (X) may also be useful in generating cyclic peptides. A cyclic peptide is a peptide whose amino and carboxyl termini are themselves linked together, forming a circular chain. The reaction would be similar to the ubiquitination reaction described earlier. The C-terminus end of a peptide is converted into a thioester. Alternatively, a sidechain of an amino acid in the peptide has a thioester end. A pyrrolysine analog of Formula (I) or (X) is also incorporated into the peptide. The thioester end reacts with the cysteine-like free end of the pyrrolysine analog of -continued

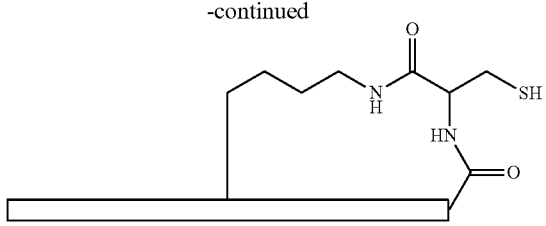

Alternatively, it is contemplated that a cyclic portion could be formed within a protein if the pyrrolysine analog is reacted with an amino acid that has a thioester end.

It is also contemplated that some pyrrolysine analogs could be used as inhibitors of deubiquitinases. In particular, deubiquitinase typically cleaves an amide bond. Analogs which do not contain an amide bond cannot be cleaved and are stable inside the cell.

The following examples illustrate compounds and methods according to the methods of the present disclosure. The examples are merely illustrative and are not intended to limit the present disclosure with regard to the materials, conditions, or process parameters set forth therein.

EXAMPLES

Example 1

Two analogs corresponding to Formulas (1) and (2) were prepared and tested for readthrough efficiency. Formula (1) is the (S,S)-isomer and Formula (2) is the (R,S)-isomer, and are shown again below.

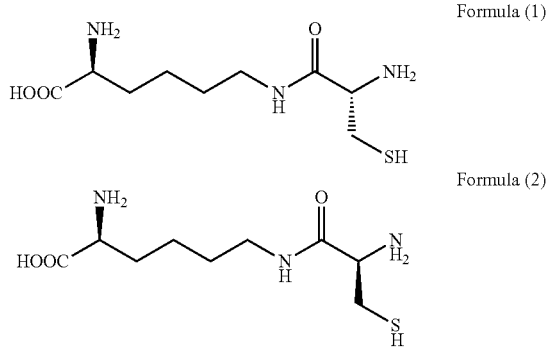

The (S,S)-isomer was prepared by coupling (BOP/NMM) the N,S-protected cysteine with Boc-Lys-OtBu to provide the amide in excellent yield (98%) (step a). Its full deprotection with TFA/Et3SiH furnished the (S,S)-isomer as its TFA salt (step b). Its diastereomer (R,S)-isomer was prepared in an analogous manner.

Synthesis of (S,S)-isomer pyrrolysine analog: Step a) Boc-Lys-OtBu, BOP, NMM, $CH_2Cl_2$, RT, 48 hrs, yield 98%; Step b) TFA, $Et_3SiH$, $CH_2Cl_2$, RT, 3 hrs, yield ca. 100%. Abbreviations: BOP: (benzotriazol-1-yloxy)tris(dimethylamino) phosphoni-umhexafluorophosphate, NMM: N-methylmorpholine, TFA: trifluoroaceticacid, Trt: trityl, Boc: tert-butoxycarbonyl.

In order to evaluate the UAG codon readthrough efficiency for the two diastereomers, the brightly emitting red fluorescent protein, mCherry, was employed as a reporter. Briefly, the Lys55 codon of this protein was site-specifically mutated to UAG and inserted into the plasmid pPylST harbouring the pyrrolysine tRNA (PylT) and synthetase (PylS) genes. *E. coli* strain BL21(DE3) transformed with this plasmid was grown in the Terrific Broth medium supplied with either the (S,S)-isomer or (R,S)-isomer at varying concentrations. The results of the mCherry readthrough assays demonstrated that the presence of either (S,S)-isomer or (R,S)-isomer enabled readthrough of the UAG codon, with the (S,S)-isomer serving as a much better substrate in terms of readthrough efficiency. This is seen in the graph of FIG. 1, where the relative fluorescence of the (S,S)-isomer was higher at all concentrations.

The ability to generate a site-specifically ubiquitinated protein in a single ligation step from two genetically encoded segments was then demonstrated by taking advantage of the (S,S)-isomer pyrrolysine analog of Formula (1). For our model studies, we chose calmodulin, CaM, a small 17 kDa protein that plays a central role in calcium signalling in eukaryotes.

Figure 2:
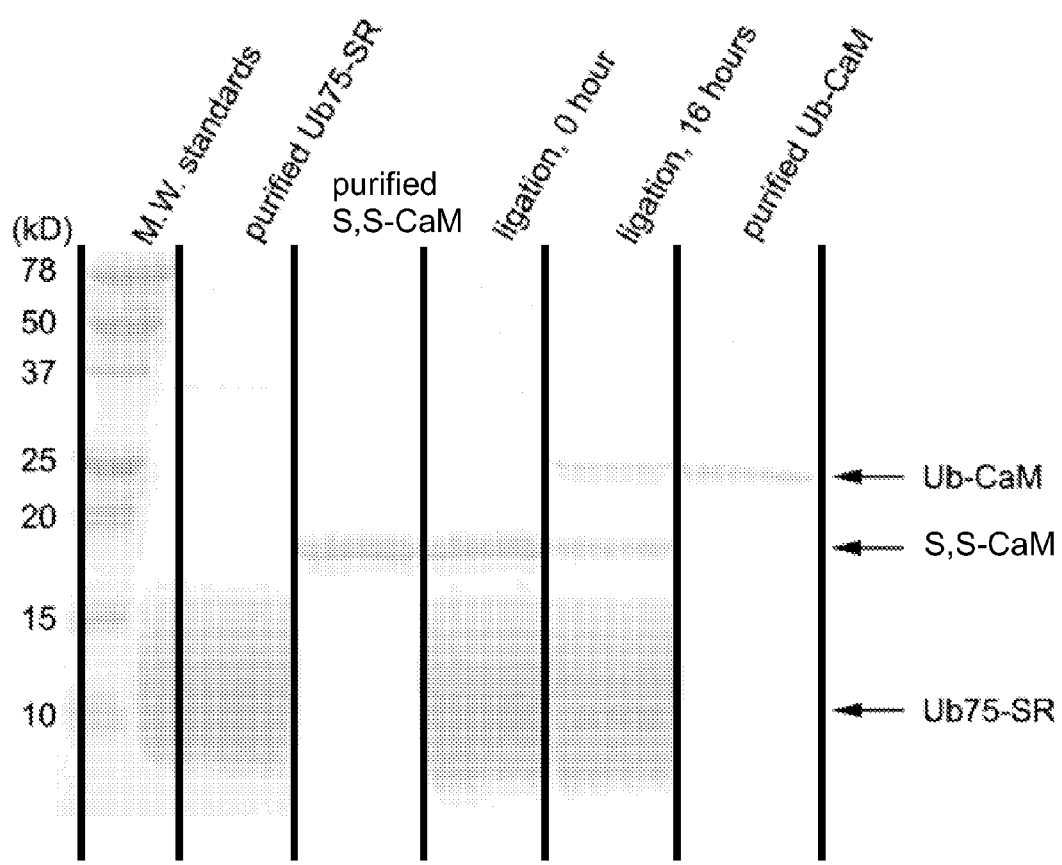
FIG. 2 is an SDS-PAGE gel showing the site-specific ubiquitination of calmodulin at a location determined by a pyrrolysine analog.

To generate (S,S)-isomer-containing CaM ((S,S)-CaM), *Rattus norvegicus* CaM (Lys21Pyl) was subcloned into pPylST. The recombinant protein (S,S)-CaM was produced and purified by hydrophobic-interaction chromatography. Significantly, MALDI-TOF MS analysis of the purified product demonstrated that the reactive Cysteine-mimicking residue of the pyrrolysine analog remained intact throughout expression in a cellular system. The truncated *Homo sapiens* ubiquitin containing residues 1 to 75 (Ub75) was produced as a Ub75/intein/CBD (chitin-binding domain) fusion protein and purified by chitin affinity chromatography. On-column thiolysis was initialized with sodium 2-mercaptoethane sulfonate (MESNa) to generate the Ub75 thioester (Ub75-SR) which was mixed with (S,S)-CaM in a 5:1 molar ratio to promote NCL. The reaction mixture was incubated at room temperature overnight, and the ubiquitinated calmodulin (Ub-(S,S)-CaM) product was isolated from unreacted Ub75-SR and (S,S)-CaM via anion exchange chromatography. Approximately 30% of (S,S)-CaM was converted to ubiquitinated calmodulin. The identity of the ligation product was confirmed by MALDI-TOF mass spectrometry and tandem mass spectrometry. FIG. 2 is a SDS-PAGE gel showing the starting materials, the ligation mixture at two time points, and the purified ligation product.

Ubiquitinated CaM has been reported to have a reduced affinity for phosphorylase kinase as well as a decreased maximal degree of activation compared to wild-type CaM. The prepared ubiquitinated CaM activation towards protein phosphatase 2B, the only known protein phosphatase whose activity is regulated by CaM, was measured. In this case, no change of CaM activity was observed upon ubiquitination.

Example 2

Pyrrolysine analogs of Formulas (C1), (3), (4), (5), (6), and (7) were prepared and used to carry out UAG readthrough experiments. These analogs are reproduced again below.

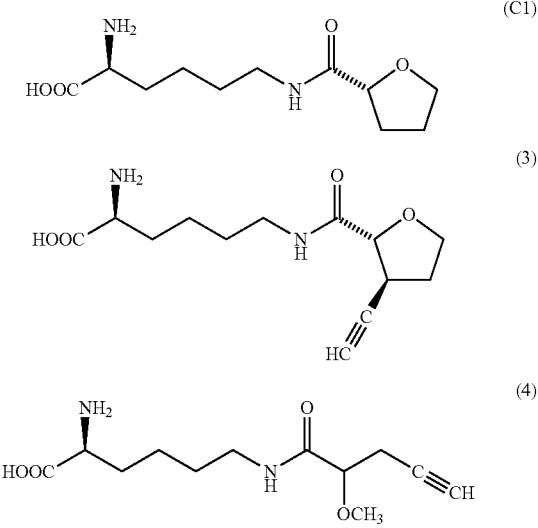

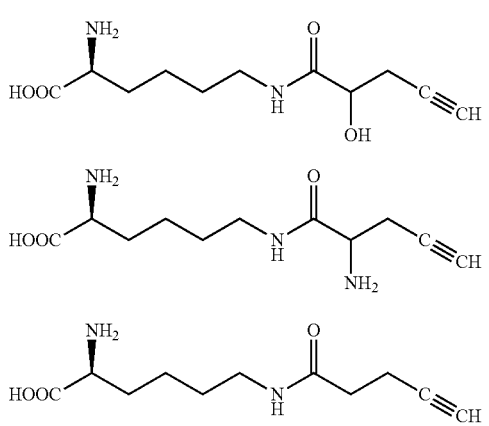

Preparation of the analog C1 has been previously described. Preparation of analog 3 was previously described in *Angew. Chem. Int. Ed.* 2009, 48, pp. 1633-1635.

The requisite pyrrolysine analogs 4-7 were prepared by coupling (BOP/NMM) the corresponding pent-4-ynoic acids with Boc-Lys-OtBu to give amides in excellent yield (>90%) in each case. Their subsequent treatment with neat TFA provided the desired pyrrolysine analogs as TFA salts.

Synthesis of pyrrolysine analogs 4-7: Step a) Boc-Lys-OtBu, BOP, NMM, CH$_2$Cl$_2$, RT, 48 hrs; Step b) TFA, RT, 1 hr, ~100%.

The site-specific incorporation efficiencies of these analogs were measured with a modified fluorescence protein assay using a fluorescent protein as a reporting gene to monitor stop codon readthrough. This approach was made compatible with large scale measurements by 1) using mCherry instead of GFP to reduce the fluorescence background introduced by growth medium, 2) growing the host cells in 24-well plates to facilitate handling of multiple samples and minimize deviation between samples, and 3) measuring the fluorescence intensity of the cell culture in the plates to save the labor of electrophoresis and western blotting.

Figure 3:
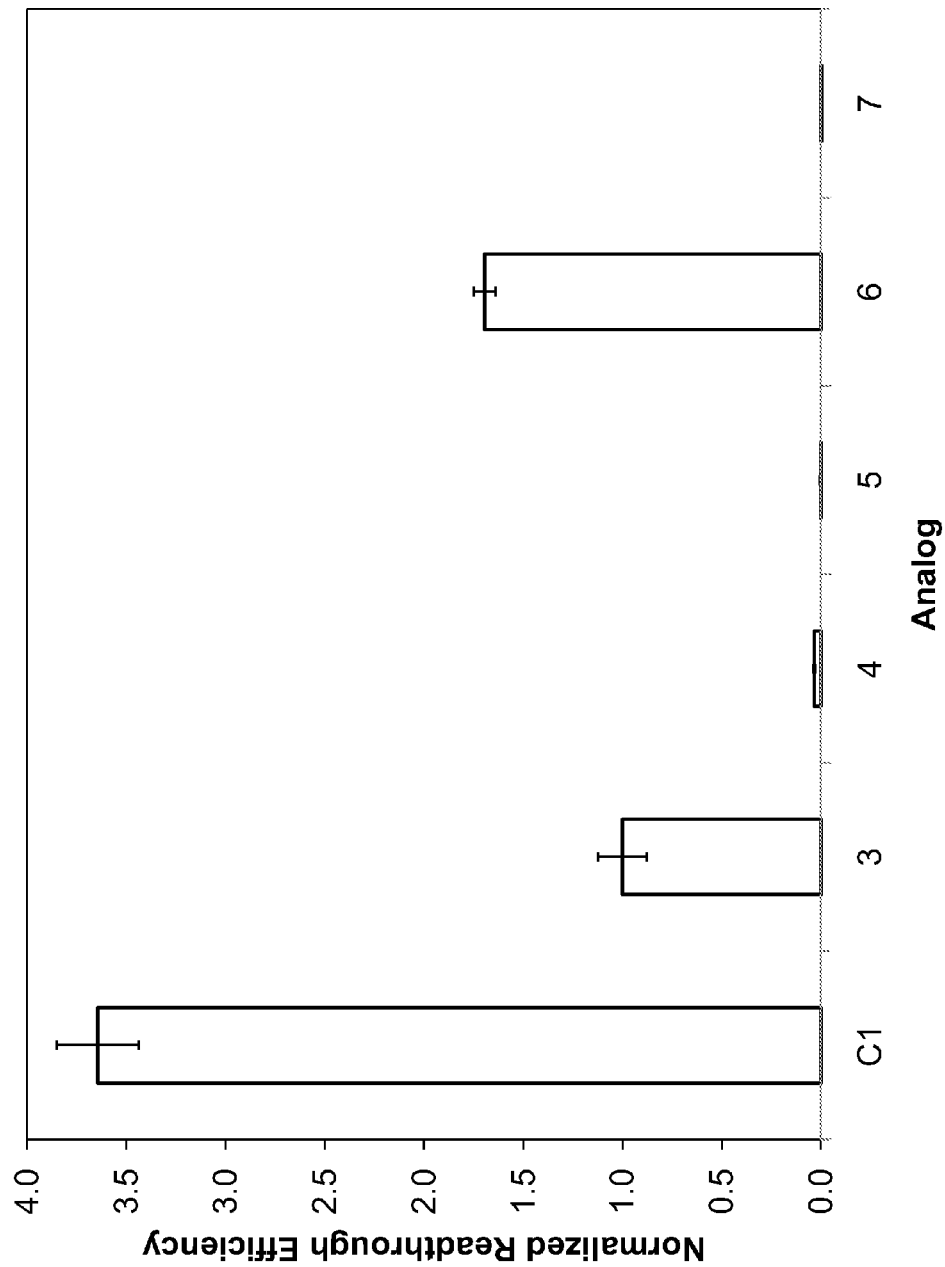
FIG. 3 is a graph comparing the readthrough efficiency of four pyrrolysine analogs of the present disclosure against two control analogs.

In this study, the Lys55 codon of mCherry was site-specifically mutated to UAG and inserted into the plasmid pPylST harbouring the pyrrolysine tRNA (PylT) and synthetase (PylS) genes from *Methanosarcina mazei*. *E. coli* strain BL21 (DE3) transformed with this plasmid was grown in the Terrific Broth medium supplied with 2 mM pyrrolysine analog to be examined. The results demonstrated dramatic difference among these analogs: 5 and 7 promoted no detectable mCherry production; 4 was 30-fold less efficient than the original clickable analog 3; 6, however, was 69% more efficient than 3. These differences are seen in FIG. 3, where the results have been normalized against analog 3. Similar results were observed when the supplied analog concentration varied from 0.5 mM to 20 mM.

Figure 4:
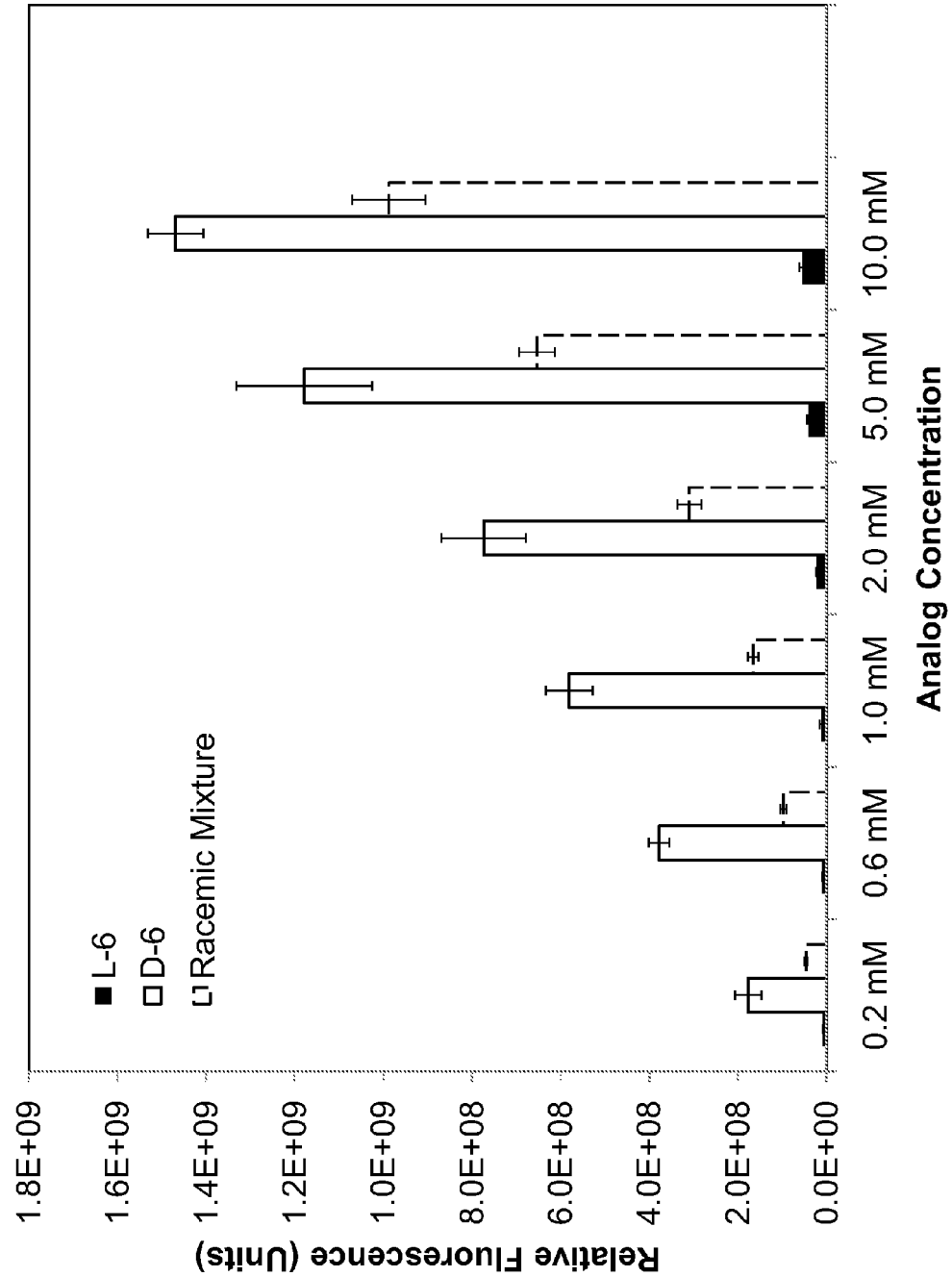
FIG. 4 is a graph comparing the readthrough efficiency of two isomers of a pyrrolysine analog, and the enantiomeric mixture, as described herein.

These preliminary screening experiments indicated that the analog 6 was the best substrate in terms of the readthrough efficiency among the four compounds tested. As analogs 4-6 were prepared and screened as ~1:1 mixtures of diastereomers, we carried out further readthrough experiments with isomerically pure samples of 6 prepared from commercially available (R)- and (S)-propargylglycines. The readthrough efficiencies of L-6, D-6 and the enantiomer mixture were tested at various concentrations. The results showed D-6 was 35-fold more efficient than L-6, while the mixture displayed a moderate efficiency. This is seen in FIG. 4. Notably, the optically pure D-6 was more efficient than the mixture with twice the concentration, which should contain the same amount of D-6. One explanation is that the less efficient incorporable isomer L-6 is a competitive inhibitor of D-6.

The observation of much higher readthrough efficiencies for the D-amino acid was notable, since the R-stereocenter in D-6 matches that of pyrrolysine, while the amine group of D-6 would be expected to adopt a similar position to the imine nitrogen of pyrrolysine.

Based on previous studies, it was hypothesized that while an imine would be deprotonated at physiological pH (pH=7), an amine group would be primarily protonated, hindering its ability to serve as a proton acceptor. However, at slightly higher pHs (i.e. more alkaline), the amine would be become deprotonated and thus the readthrough efficiency of D-6 would be expected to increase.

Figure 5:
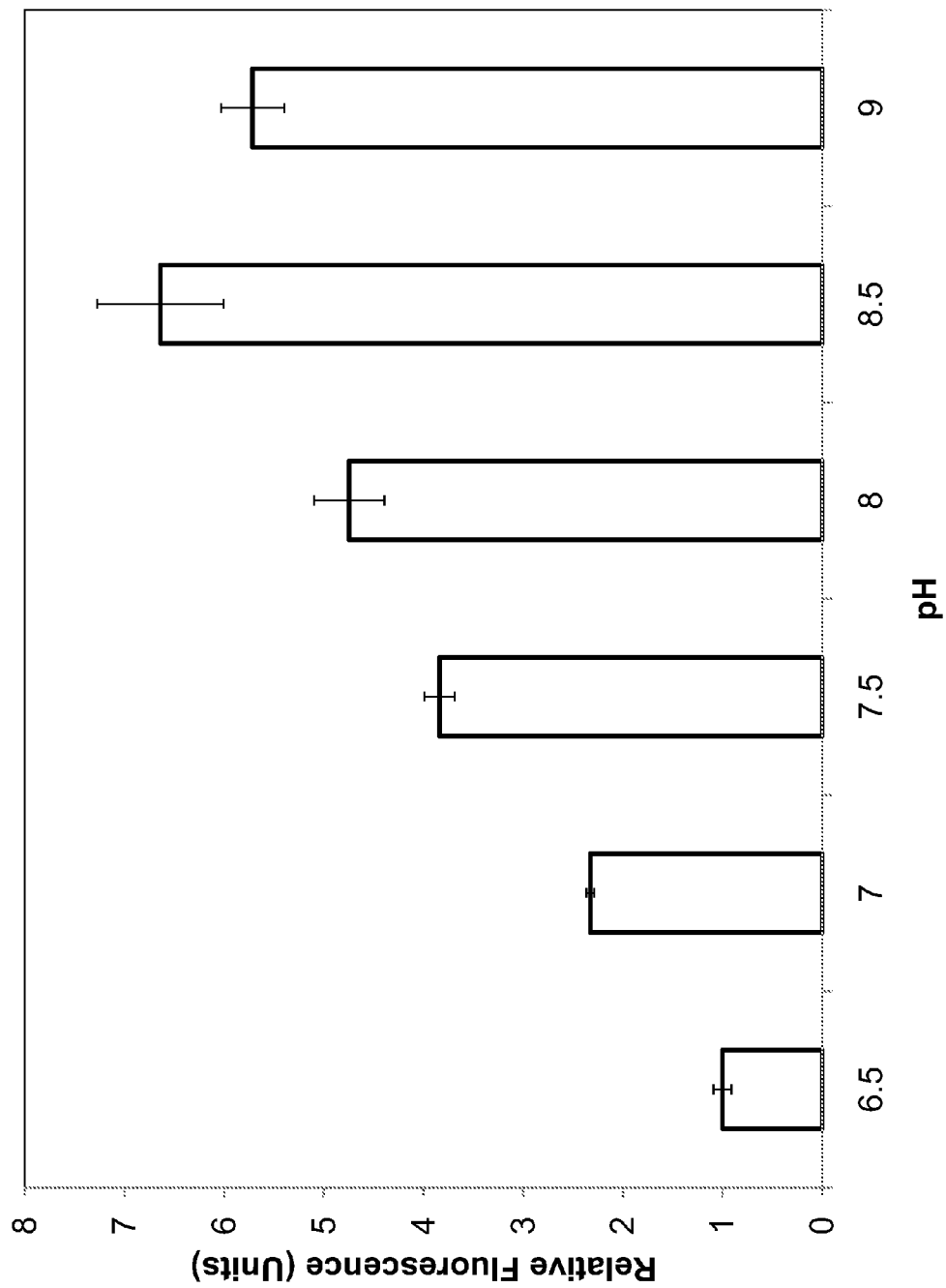
FIG. 5 is a graph showing the readthrough efficiency of an isomer of a pyrrolysine analog versus pH, as described herein.

The effect of the growth medium pH on the readthrough efficiency of D-6 was investigated using the modified mCherry assay. As anticipated, the pH had a dramatic effect. When 2 mM D-6 was used as substrate, the production of full-length mCherry increased as the pH of the growth medium increased. The total amount of produced mCherry peaked at pH 8.5 and dropped a little at pH 9.0 due to a lower cell density. These results are seen in FIG. 5.

To test the taggability of D-6, calmodulin (CaM) incorporated with D-6 at amino acid position 34 were prepared. About 40 mg of D-6-CaM can be purified from 1 L growth medium supplied with 2 mM D-6, which was a high yield. D-6-CaM was then treated with azidocoumarin in the presence of CuSO$_4$, ascorbate, diazole and HEPES buffer (pH 8.0) at room temperature.

Figure 6:
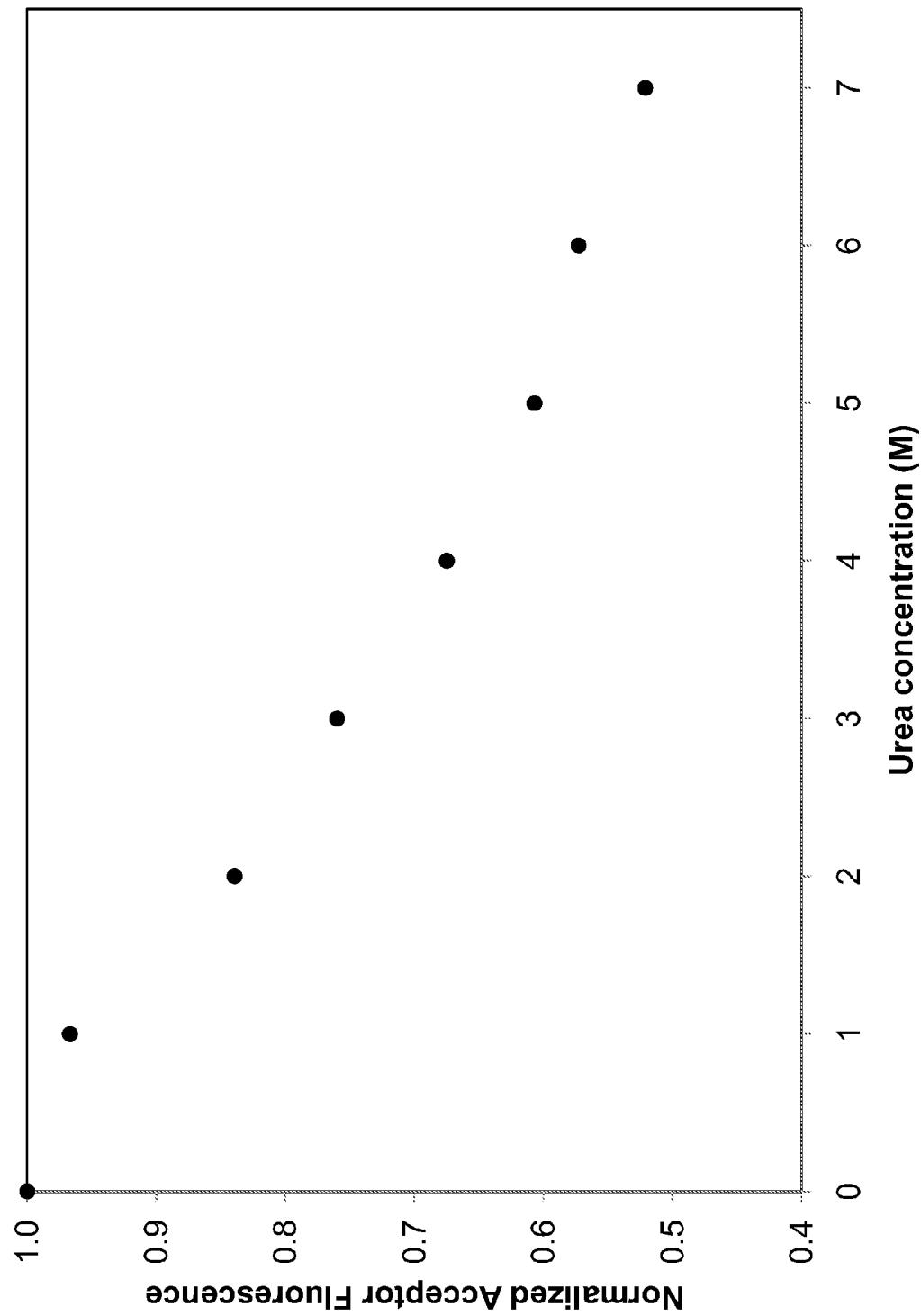
FIG. 6 is a graph showing the suitability of labeling using a pyrrolysine analog for protein denaturation studies, as described herein.

We prepared doubly-labeled CaM for use with intramolecular Förster resonance energy transfer (FRET) experiments which require site-specific incorporation of two fluorescent dyes. CaM is a model system for the study of multi-domain protein unfolding, and its shape elongation induced by denaturant urea has been previously observed. We prepared doubly-labeled CaM by labeling the residue 34, D-6, with fluorescence donor azidocoumarin, and labeling Cys114 with the fluorescence acceptor BODIPY® FL N-(2-aminoethyl)maleimide. To test the suitability of our labeling method for protein denaturation studies, the doubly-labeled CaM was incubated with 0-7 M urea. The subsequent fluorescence measurements, shown in FIG. 6, clearly reveal a loss of fluorescence intensity of the acceptor that can be attributed to the unfolding of the CaM protein.

Example 3

The pyrrolysine analog of Formula (10), having a terminal azide group was prepared as shown below:

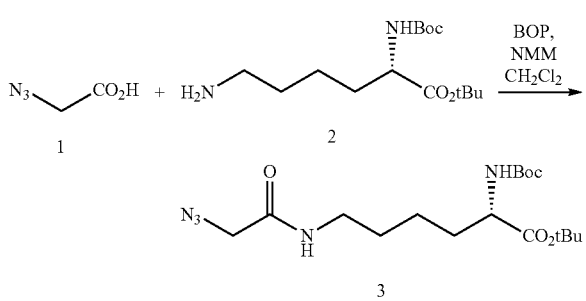

tert-Butyl N$^2$-(tert-butoxycarbonyl)-N$^6$-(azidoacetyl)lysinate (1)

To a solution of acid 1 (270 mg, 2.05 mmol) and Boc-Lys-OtBu 2 (619 mg, 2.05 mmol) in CH$_2$Cl$_2$ (10 mL) was added N-methylmorpholine (NMM, 495 μL, 4.51 mmol) followed by benzotriazol-1-yloxy)tris(dimethylamino)phosphonium hexafluorophosphate (BOP, 997 mg, 2.26 mmol). The reaction mixture was stirred at room temperature for 17 hrs and then diluted with brine (10 mL). The phases were separated and the extraction was completed with additional portions of $CH_2Cl_2$. The combined extracts were dried ($MgSO_4$), and evaporated in vacuo to give a brown oil. Purification by flash chromatography (silica gel; hexanes/EtOAc, 1/1) gave the title compound 3 (702 mg, 89%) as a clear oil.

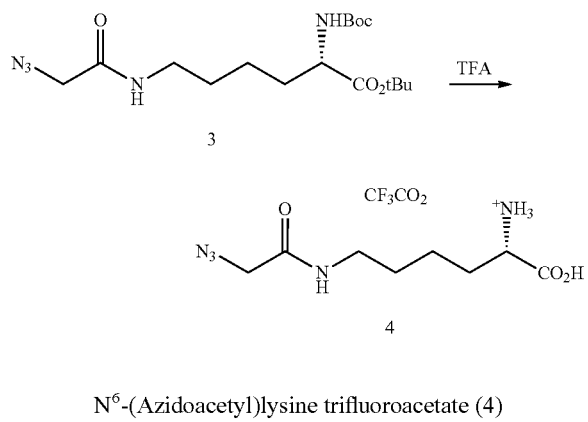

$N^6$-(Azidoacetyl)lysine trifluoroacetate (4)

A solution of the lysine derivative 3 (360 mg, 0.94 mmol) in TFA (5 mL) was stirred at room temperature for 2 hrs and then evaporated in vacuo. The residue was co-evaporated four times with MeOH (4×5 mL) to give the title compound 4 (325 mg, ~100%) as a clear oil.

Example 4

The pyrrolysine analog of Formula (9), having a terminal isocysteine group was prepared as shown below:

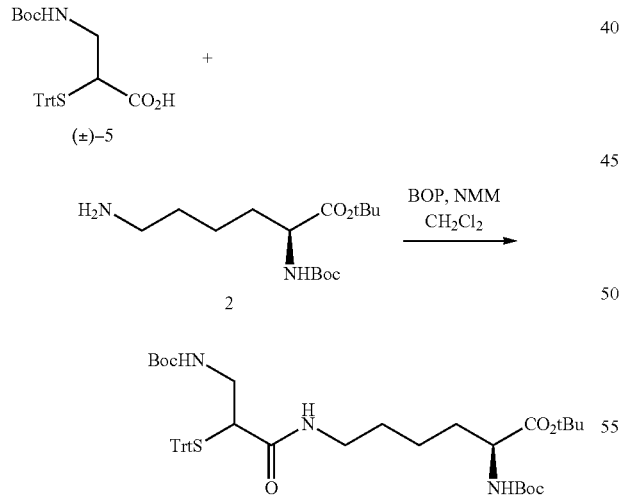

t-Butyl $N^2$-(tert-butoxycarbonyl)-$N^6$—((R/S)-3-tert-butoxycarbonylamino-2-(tritylthio)propanoyl)lysinate ((R/S,S)-6)

To a solution of racemic Boc-iCys(Trt)-OH (±)-5 (1.63 g, 3.52 mmol) and Boc-Lys-OtBu 2 (1.06 g, 3.52 mmol) in $CH_2Cl_2$ (20 mL) was added NMM (850 μL, 7.74 mmol) followed by BOP (1.71 g, 3.87 mmol). The reaction mixture was stirred at room temperature for 17 hrs and diluted with saturated $NaHCO_3$ (20 mL). The phases were separated and the extraction was completed with additional portions of $CH_2Cl_2$. The combined extracts were dried ($MgSO_4$), and evaporated in vacuo to give a yellow oil. Purification by flash chromatography (silica gel; hexanes/EtOAc, 3/1→EtOAc) gave the title compound (R/S,S)-6 (2.10 g, 80%) as a white foam.

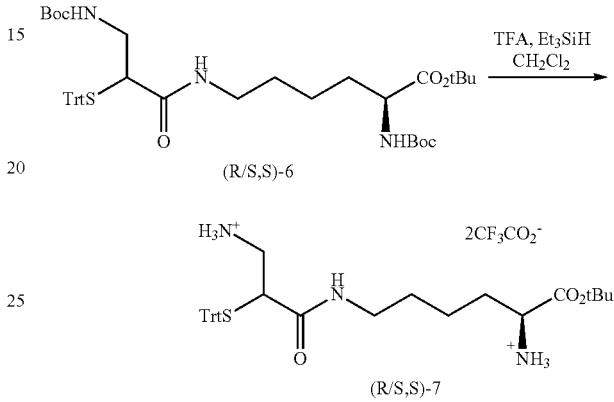

$N^6$-((R/S)-3-Amino-2-mercaptopropanoyl)lysine ditrifluoroacete ((R/S,S)-7)

To a solution of amide (R/S,S)-6 (500 mg, 0.67 mmol) in $CH_2Cl_2$ (8.5 mL) was added $Et_3SiH$ (0.5 mL, 3 mmol) followed by trifluoroacetic acid (TFA, 7.9 mL). The initially developed yellow color disappeared within a few seconds and the colorless reaction mixture was stirred at room temperature for 3 hrs. The volatiles were evaporated in vacuo and the glue-like residue that was suspended in $Et_2O$ (10 mL). The $Et_2O$ layer was carefully removed and the residue was washed three more times with fresh portions of $Et_2O$. The residue was then dried in vacuo to give the title compound ((R/S,S)-7 (285 mg, ~100%) as a clear oil.

Example 5

The pyrrolysine analog of Formula (11), having a diazirine moiety, was prepared as shown below:

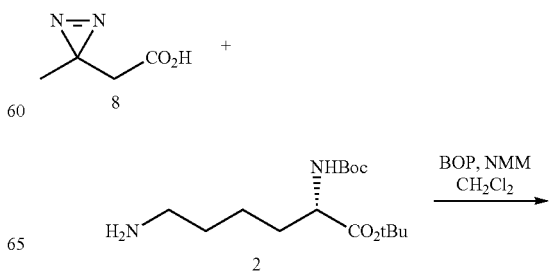

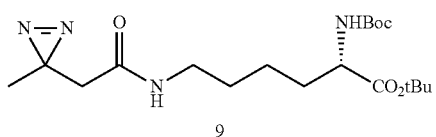

tert-Butyl N²-(tert-butoxycarbonyl)-N⁶-(2-(3-methyl-3H-diazirin-3-yl)acetyl)lysinate (9)

To a solution of acid 8 (1.14 g, 10.0 mmol) and Boc-Lys-OtBu 2 (2.41 g, 7.98 mmol) in CH₂Cl₂ (70 mL) was added N-methylmorpholine (NMM, 2.4 mL, 22 mmol) followed by benzotriazol-1-yloxy)tris(dimethylamino)phosphonium hexafluorophosphate (BOP, 4.86 g, 11.0 mmol). The reaction mixture was stirred at room temperature for 18 hours and then diluted with brine (70 mL). The phases were separated and the extraction was completed with additional portions of CH₂Cl₂. The combined extracts were dried (MgSO₄), and evaporated in vacuo to give an orange oil. Purification by flash chromatography (silica gel; hexanes/EtOAc, 1/1 EtOAc) gave the title compound 9 (3.34 g, 84%) as a clear oil.

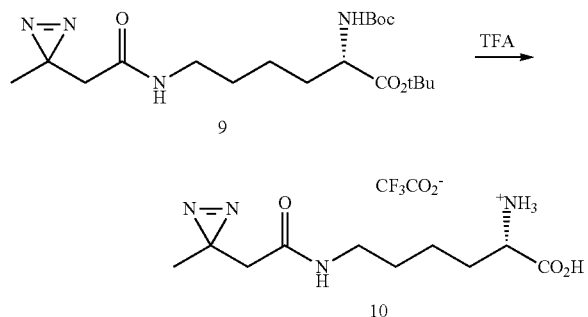

N⁶-(2-(3-Methyl-3H-diazirin-3-yl)acetyl)lysine trifluoroacetate (10)

A solution of the lysine derivative 9 (174 mg, 0.44 mmol) in TFA (1.4 mL) was stirred at room temperature for 45 minutes and then evaporated in vacuo. The residue was co-evaporated four times with MeOH (4×5 mL) and to give the title compound 10 (160 mg, ~100%) as a brown oil that was used in the subsequent biochemical studies without any further purification.

The compound 10 was successfully synthesized and incorporated into a recombinant protein.

Example 6

SUMOylation of a target protein, TDG, was performed. Generally, a pyrrolysine analog corresponding to Formula (2) was incorporated into TDG and the recombinant protein was SUMOylated.

Intein technology was used to generate a thioester linkage at the C-terminus of the SUMO1 protein.

SUMO1 was cloned into pTXB1 vector bearing a GyrA intein with a chitin binding domain and His tag at its C-terminus end. The last residue of SUMO1, glycine, was directly conjugated to a N-terminal cysteine on the intein. Expression of the resulting clone was carried out in BL21 pLys by induction at 37° C. using 0.05 mM isopropyl β-D-1-thiogalactopyranoside (IPTG). Expressed SUMO-intein was treated with sodium salt of mercaptoethane sulfonic acid (MESNa; 200 mM) in 10 mM phosphate buffer (pH 8.0) and 200 mM NaCl to generate the thioester form of SUMO1 and purified using affinity Ni His60 column (Clontech) and Sephadex G75 gel filtration column (GE Healthcare).

Expression of thymidine N-glycolsylase (TDG) bearing the analog of Formula (2) was carried out by inducing BL21 pLys in the presence of 0.1 mM IPTG and 10 mM analog at 37° C. for 6 hours. TDG bearing His tag was bound to Ni⁺² affinity resin and the ligation reaction was performed with SUMO1 (1:10 molar ratio of TDG to SUMO1) in 10 mM phosphate (pH 8.0) and 200 mM NaCl and 30 mM MESNa and 10 mM tris(2-carboxyethyl)phosphine (TCEP) for 3 hours at room temperature. A band corresponding to the expected ligation product of SUMO1-TDG was observed on SDS-PAGE gel.

Example 7

SUMO1 was biotinylated using a pyrrolysine analog, YPY4, corresponding to Formula (6).

The glutamate (E) at position 75 of the human SUMO1 was mutated to a UAG codon for the subsequent incorporation of the pyrrolysine analog, YPY4, into the SUMO1 protein. The E. coil BL21(DE) harboring a plasmid for inducible expression of this mutant human SUMO1 (E75Pyl) was grown in 1 liter of lysogeny broth (LB) at 37° C. Cells were induced with 1 mM IPTG and supplemented with 5 mM YPY4 and 25 mM Tris-HCl pH 8.5 at OD=0.6. Cells were harvested after 4 hrs of additional growth. The purified mutant SUMO1 proteins were then used to SUMOylate human peroxiredoxin (PDRX) proteins in vitro at 37° C. for 3 hrs.

The SUMO1-PDRX conjugates were isolated via MBP purification. Biotinylated of the SUMO1-PRDX conjugates were carried out by reacting a biotin-azide (Invitrogen) with the YPY4 on residue position 75 of SUMO1 via click chemistry. The biotinylated SUMO1-PDRX conjugates were isolated by binding the proteins to the monomeric avidin agarose. Elutions from the avidin agarose using 4 mM biotin, and 0.1M glycine pH 2.8 with 8M urea were collected, respectively, and were then subjected to in-gel trypsin digestion. MALDI was used to screen for the fractions containing digested peptides with molecular weight greater than 3000 daltons. The identified peptides were then subjected to LC/MS-MS to deduce the amino acid compositions.

Example 8

Exemplary schemes for obtaining the ketone/aldehyde analogs of Formulas (XIII)-(XV) are presented below.

A dioxolane-containing analog 14 can be prepared in at least two ways. First, an acid 11 can be coupled with a protected lysine 2. Alternatively, terminal alkene analog 13 can be oxidatively converted to analog 14.

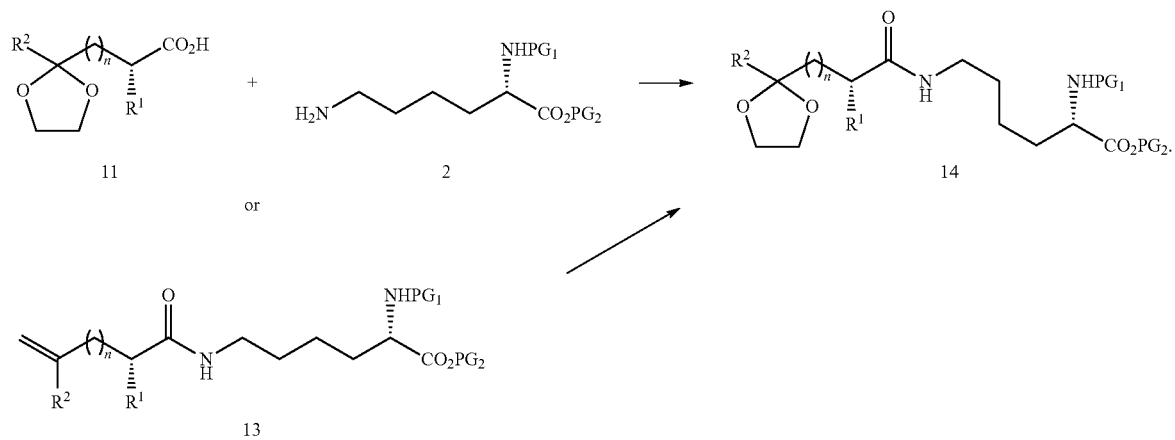

After being deprotected, dioxolane analog 15 can be treated with an acid to give an aldehyde or ketone analog 16. Here, in some embodiments, n is 0 to 8; $R^1$ is hydrogen or amino; and $R^2$ is hydrogen or alkyl.

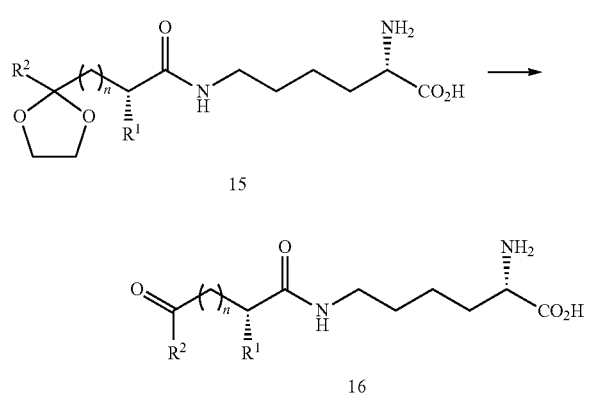

Example 9

An exemplary schemes for obtaining the malonate analog of Formula (13) is shown below. Protected malonate analog 18 can be obtained by coupling between a mono-protected malonate 17 and a lysine derivative 2. Deprotonation of the protecting groups leads to malonate analog 19. Typically, protecting groups $PG_1$ and $PG_2$ are selectively deprotonated, leaving $PG_4$ (not shown). Following incorporation, PG4 is deprotonated with an acid, resulting in decarboxylation and formation of acetyl-lysine 14 (not shown).

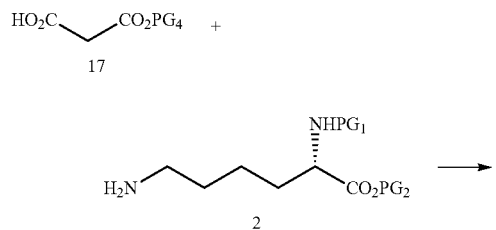

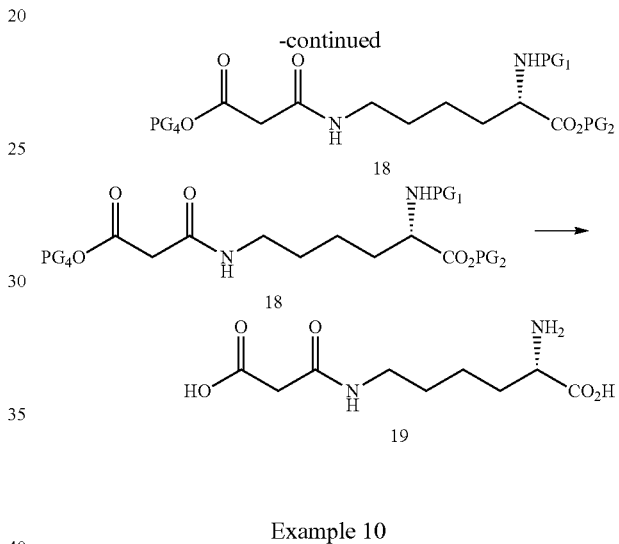

Example 10

An exemplary schemes for obtaining the thiazolidine-containing analogs of Formulas (XVI) and (XVII) is shown below. Thiazolidine-containing analog 23 can be obtained by coupling protected thiazolidine-2-carboxylate 21 with a protected lysine 2 to produce intermediate 23 followed by deprotection of the protecting groups.

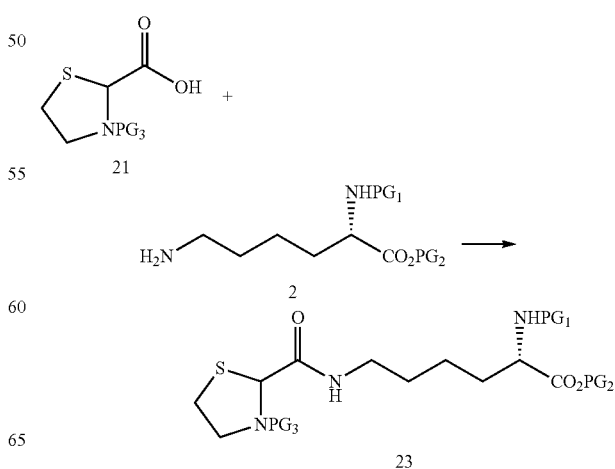

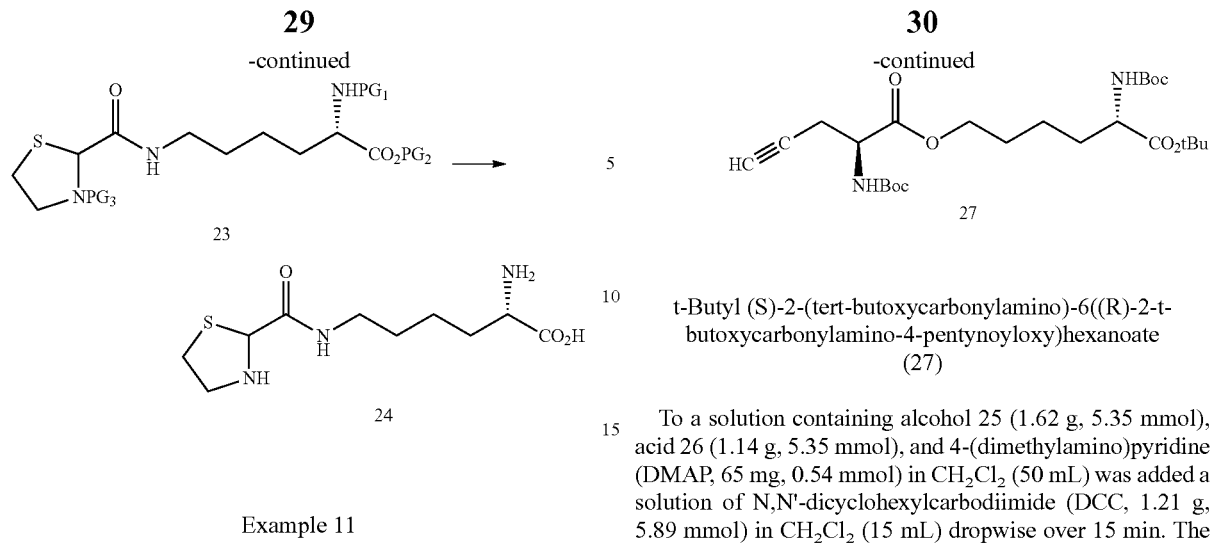

Example 11

The pyrrolysine analog of Formula (15) was prepared as shown below:

t-Butyl (S)-2-(tert-butoxycarbonylamino)-6-hydroxyhexanoate (25)

A vigorously stirred solution of Boc-Lys-OtBu 2 (6.20 g, 20.5 mmol) in water (120 mL) and dioxane (60 mL) was warmed to 65° C. and treated with sodium nitroprusside (SNP, $Na_2[Fe(CN)_5NO] \cdot 2H_2O$) (9.8 g, 33 mmol) portionwise over 1 hour. The reaction mixture was stirred at 65° C. for an additional 4 hours while its pH was maintained at 9-10 by addition of 2M NaOH. It was then cooled to room temperature and filtered through a pad of CELITE. The filtrate was extracted with EtOAc (6×100 mL) and the combined extracts were dried ($MgSO_4$), filtered, and evaporated in vacuo to give a purple oil. Its purification by flash chromatography (silica gel; hexanes/EtOAc, 8/1→3/7) gave the title compound 25 (2.28 g, 37%) as a clear oil.

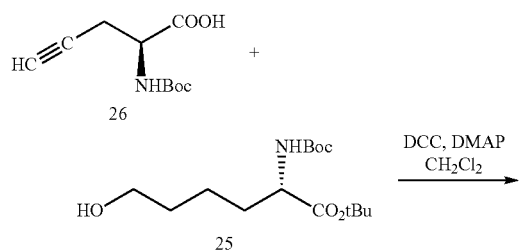

t-Butyl (S)-2-(tert-butoxycarbonylamino)-6-((R)-2-t-butoxycarbonylamino-4-pentynoyloxy)hexanoate (27)

To a solution containing alcohol 25 (1.62 g, 5.35 mmol), acid 26 (1.14 g, 5.35 mmol), and 4-(dimethylamino)pyridine (DMAP, 65 mg, 0.54 mmol) in $CH_2Cl_2$ (50 mL) was added a solution of N,N'-dicyclohexylcarbodiimide (DCC, 1.21 g, 5.89 mmol) in $CH_2Cl_2$ (15 mL) dropwise over 15 min. The resulting suspension was stirred at room temperature for 15 hrs, evaporated in vacuo, re-suspended in EtOAc (40 mL), and passed through a plug of CELITE. The filtrate was evaporated in vacuo to give a yellow oil that was purified by flash chromatography (silica gel; hexanes/EtOAc, 3/7) providing the title compound 27 (2.31 g, 87%) as a clear oil.

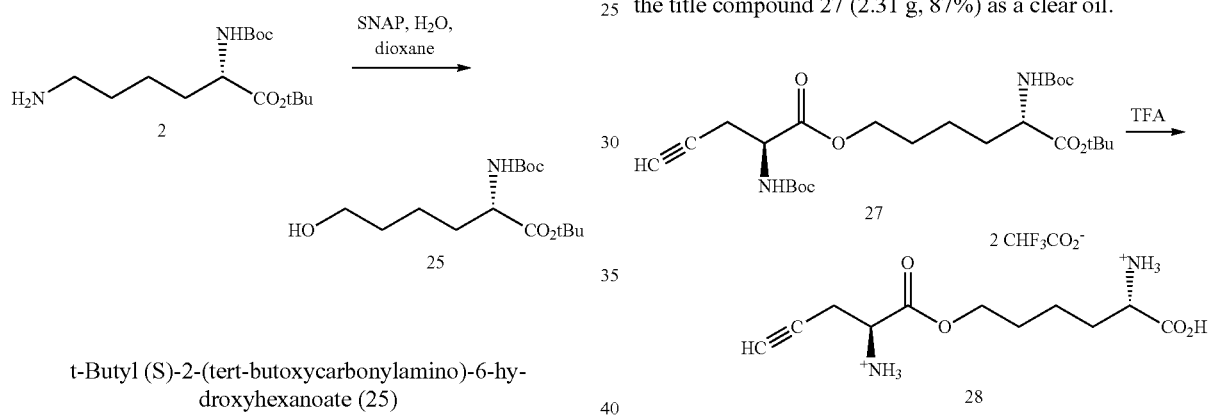

(S)-2-Amino-6-((R)-2-amino-4-pentynoyloxy)hexanoic acid ditrifluoroacetate (28)

A solution of the protected lysine derivative 27 (1.20 g, 2.41 mmol) in TFA (10 mL) was stirred at room temperature for 2 hrs and then evaporated in vacuo. The residue was co-evaporated four times with MeOH (4×5 mL) and once with $CH_2Cl_2$ (5 mL) to give the title compound 28 (1.16 g, ~100%) as a clear oil.

Example 12

To evaluate the readthrough efficiency of the pyrrolysine analog of Formula (15), its ability to promote readthrough of an mCherry gene containing a UAG codon was tested under different conditions.

An pyIST-mCherry plasmid containing a UAG codon at residue 55 of the mcherry gene was transformed into *E. coli* BL21 (DE). A single colony was used to grow a 3-mL overnight starter culture. 120 μL of the starter culture was used to inoculate a flask of 10-mL Terrific Broth supplemented with 10 μL [50 mg/mL] of carbinicillin. Cells were grown at 37° C. with 235 rpm shaking until the $OD_{600}$ reached 1.2. The cell culture was pelleted and resuspended in 500 μL of fresh Terrific Broth. Readthrough mediated by the pyrrolysine analog was then tested in a 24-well culture plate, at analog concentrations of 0, 2, 8, and 15 mM, each of which was tested at pH 7, 7.5, 8.0, and 8.5.

Each well of the 24-well plate contained: 25 µL of the resuspended cell culture; 500 µL Terrific Broth (+0.5 µL [50 mg/mL] carbinicillin); 0.3 mM IPTG; 100 µM Tris-HCl of the appropriate pH; and the pyrrolysine analog at the appropriate concentration.

The 24-well plate containing the cell cultures was wrapped in aluminium foil and incubated at 37° C. with 80 rpm shaking for 1.5 hours. The wrapped plate was then moved to 28° C. with 160 rpm shaking for overnight growth. The amount of pyrrolysine analog uptaken into cells was quantified based on the relative florescence intensity of mCherry in each well using the GE Typhoon scanner.

Figure 7:
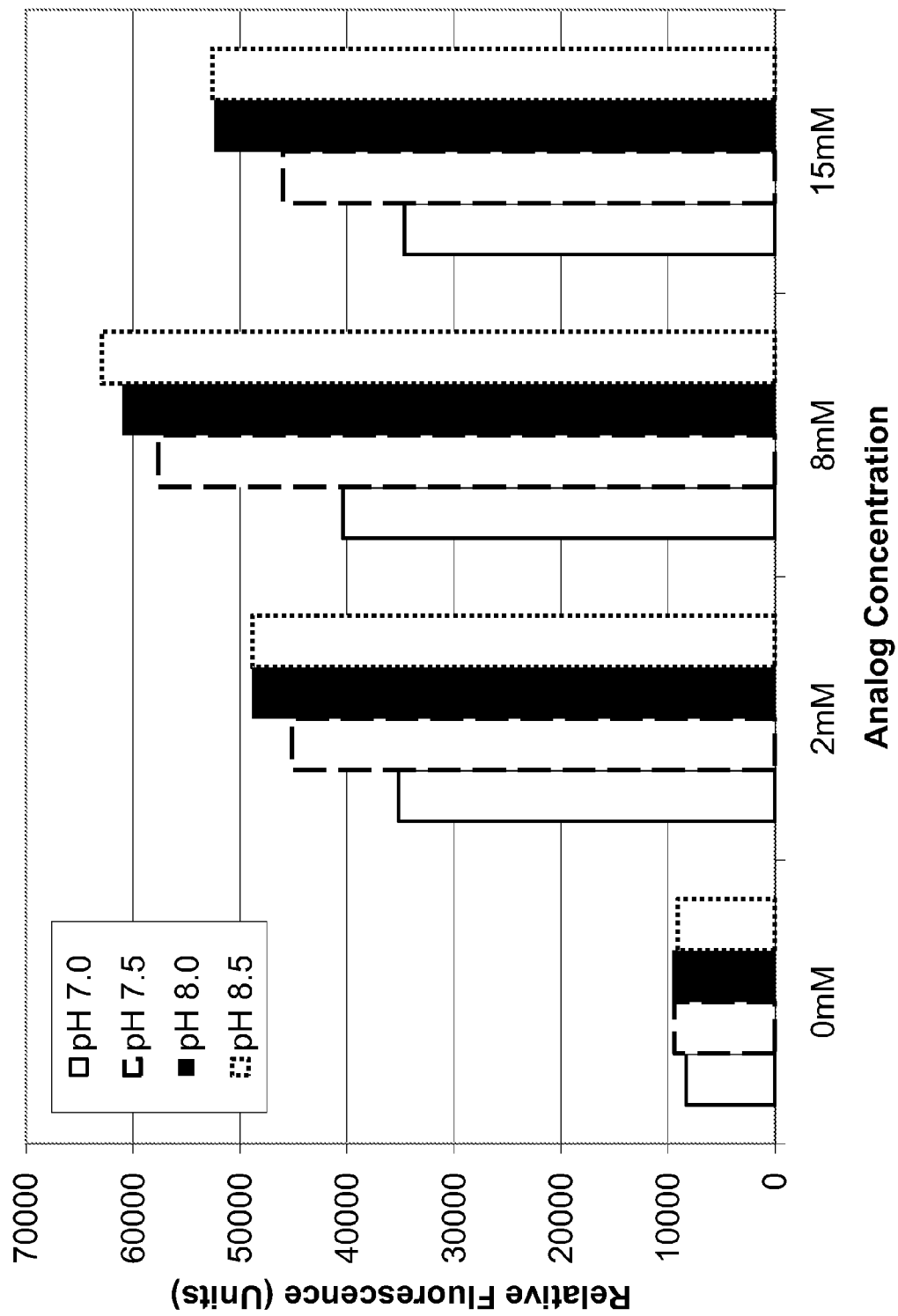
FIG. 7 is a graph showing the readthrough efficiency of a pyrrolysine analog of the present disclosure based on differences in concentration and pH.

The results are seen in FIG. 7. The optimal concentration appeared to be 8 mM.

Figure 8:
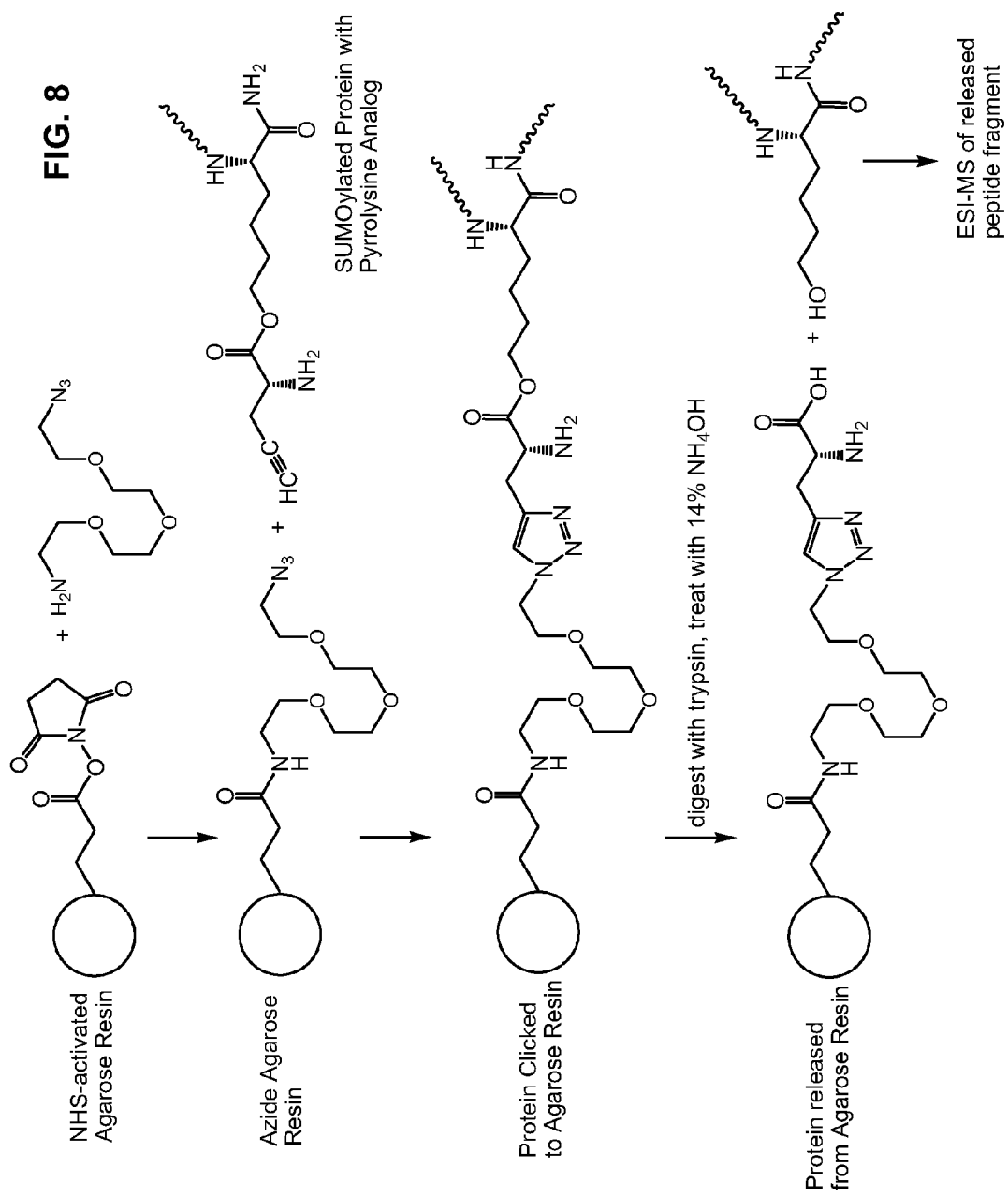
FIG. 8 is a general diagram showing how a pyrrolysine analog of the present disclosure can be used for enrichment of a targeted peptide for sequence analysis.

SUMO protein containing the pyrrolysine analog of Formula (15) was coupled to azide beads, followed by base mediated release for subsequent sequence analysis using mass spectrometry (MS). The general procedure is shown in FIG. 8.

Azide beads were prepared by coupling NHS-activated agarose (Pierce) to 11-azido-3,6,9-trioxaundecan-1-amine (Sigma). The SUMO1 protein with a stop mutation at position 75 (E75X) was overexpressed in *E. coli*. Incorporation of the pyrrolysine analog was achieved by addition of 0.2 mM IPTG. 5 mM pyrrolysine analog incorporation was reached when the $OD_{600}$ reached approximately 0.5. The cell culture was then maintained at 37° C. with 235 rpm shaking for an additional 4 hours. The analog-containing SUMO1E57X protein (SUMO1E75X) was purified using standard His-tag protein purification. SUMO1E75X protein eluted at around 100-150 mM imidizole. The purified SUMO1E75X was then coupled to the prepared azide beads using click chemistry. The coupling reaction was carried out at room temperature for 3 hours and moved to 4° C. for overnight incubation. The azide beads containing SUMO1E75X were washed extensively using HEPES pH 7.5 buffer followed by extensive wash using $ddH_2O$. 14% ammonium hydroxide solution was added to the protein-containing beads and incubated for 2 hours at room temperature. The resultant supernatant from the beads was lyophilized using speed vacuum overnight to obtain a whitish pellet. The whitish pellet was dissolved in 10 µL $ddH_2O$ and analyzed on a SDS-PAGE gel.

MS analysis identified the following peptides from SUMO when searched with massMatrix against the protein sequence:
A: IADNHTPKELGMEEEDVIEVYQE*QTGG with/without Met oxidation
B: ELGMEEEDVIEVYQE*QTGG with/without Met oxidation The "E*" denotes the glutamate residue replaced by the pyrrolysine analog. The pyrrolysine analog and the glutamate have the same mass.

The results indicated that the SUMO peptide could be trapped in an isopeptide linkage with the target protein. This would allow the SUMOylated lysinese on the target protein to be identified.

Example 13

The pyrrolysine analog of Formula (15) was prepared as shown below:

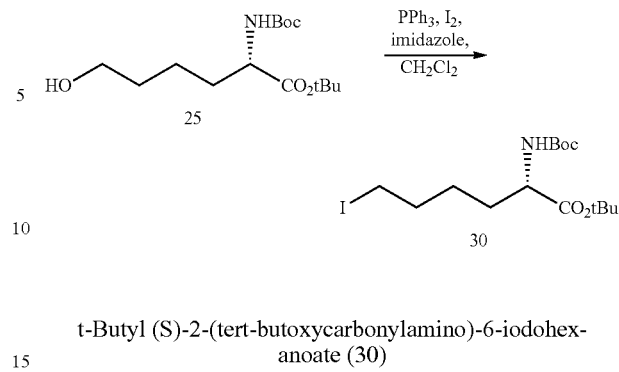

t-Butyl (S)-2-(tert-butoxycarbonylamino)-6-iodohexanoate (30)

A modified procedure described in *Tetrahedron* 2001, 57, 4759-4766 was followed. To a vigorously stirred solution of alcohol 25 (640 mg, 2.11 mmol), imidazole (359 mg, 5.28 mmol), and $PPh_3$ (1.38 g, 5.28 mmol) in $CH_2Cl_2$ (20 mL) was added with $I_2$ (1.07 g, 4.22 mmol) portionwise over 15 minutes. The resulting suspension was stirred for an additional 2 hrs and quenched with saturated $Na_2S_2O_3$ (10 mL). The phases were separated and the aqueous layer was extracted with additional portions of $CH_2Cl_2$. The combined extracts were dried ($MgSO_4$) and evaporated in vacuo. The solid residue was suspended in hexane/EtOAc (10/1 v/v, 15 mL) and the liquid decanted. This operation was performed two more times and the decanted liquid fractions were combined and evaporated in vacuo to give a yellow oil. Purification by flash chromatography (silica gel; hexanes→hexanes/EtOAc, 20/1) gave the title compound 30 (851 mg, 98%) as a clear oil.

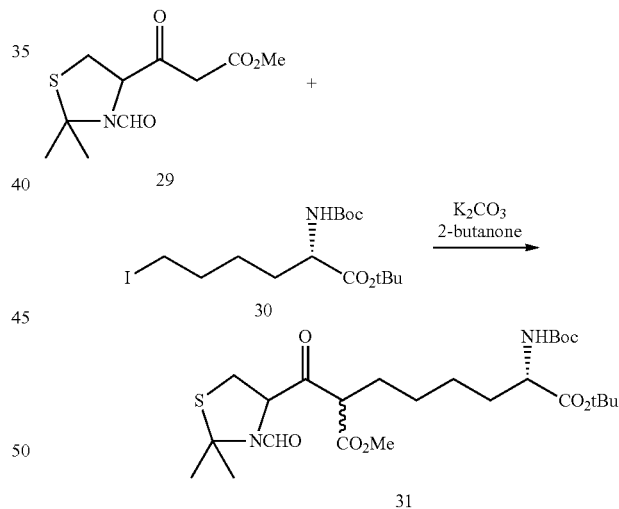

t-Butyl (2S)-2-(tert-butoxycarbonylamino)-8-(3-formyl-2,2-dimethyl thiazolidin-4-yl)-7-methoxycarbonyl-8-oxooctanoate (31)

To a solution containing ketoester 29 (258 mg, 1.05 mmol) and iodide 30 (435 mg, 1.05 mmol) in 2-butanone (20 mL) was added $K_2CO_3$ (145 mg, 1.05 mmol). The reaction mixture was refluxed for 24 hrs. The solvent was evaporated in vacuo to give a yellow residue that was dissolved in $CH_2Cl_2$ (50 mL), filtered, and evaporated in vacuo to give a yellow oil. Purification by flash chromatography (silica gel; hexanes/EtOAc, 7/3) gave the title compound 31 (401 mg, 72%) as a yellow oil.

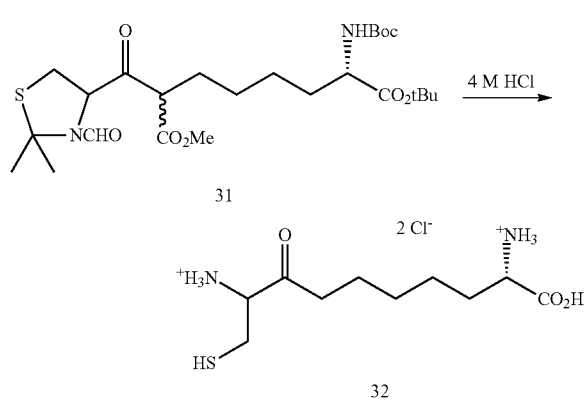

(2S)-2,9-Diamino-10-mercapto-8-oxodecanoic acid dihydrochloride (32)

A solution of ketone 31 (401 mg, 0.76 mmol) in 4M HCl (6 mL) was refluxed for 2 hrs. The reaction mixture was cooled to room temperature and evaporated in vacuo to give the title compound 32 as a yellow oil that was used in subsequent biochemical studies without any further purification.

It should be noted that the pyrrolysine analog 32 contains a ketone group instead of an amide group. Because it has a ketone, there is no amide bond that can be cleaved by deubiquitinases or other deconjugating enzymes. Thus, this pyrrolysine analog is non-hydrolyzable.

Example 14

To evaluate the readthrough efficiency of the pyrrolysine analog of Formula (16), its ability to promote readthrough of an mCherry gene containing a UAG codon was tested under different conditions.

An pylST-mCherry plasmid containing a UAG codon at residue 55 of the mcherry gene was transformed into *E. coli* BL21 (DE). A single colony was used to grow a 2-mL overnight starter culture. 150 μL of the starter culture was used to inoculate a flask of 15-mL 2XYT media supplemented with 15 μL [100 mg/mL] of carbinicillin. Cells were grown at 37° C. with 250 rpm shaking until the $OD_{600}$ reached 1.0. The cell culture was pelleted and resuspended in 750 μL of fresh 2XYT. Readthrough mediated by the pyrrolysine analog was then tested in a 24-well culture plate, at analog concentrations of 0, 5, 10, and 15 mM, each of which was tested at pH 7.0, 7.5, 8.0, 8.5, 9.0, and 9.5.

Each well of the 24-well plate contained: 25 μL of the resuspended cell culture; 500 μL 2XYT (+0.5 μL [100 mg/mL] carbinicillin); 0.3 mM IPTG; 100 mM Tris-HCl of the appropriate pH; and the non-hydrolyzable pyrrolysine analog at the appropriate concentration.

The 24-well plate containing the cell cultures was wrapped in aluminium foil and incubated at 25° C. with 180 rpm shaking for overnight growth. The amount of non-hydrolyzable pyrrolysine analog uptaken into cells was quantified based on the relative florescence intensity of mCherry in each well using the GE Typhoon scanner.

Figure 9:
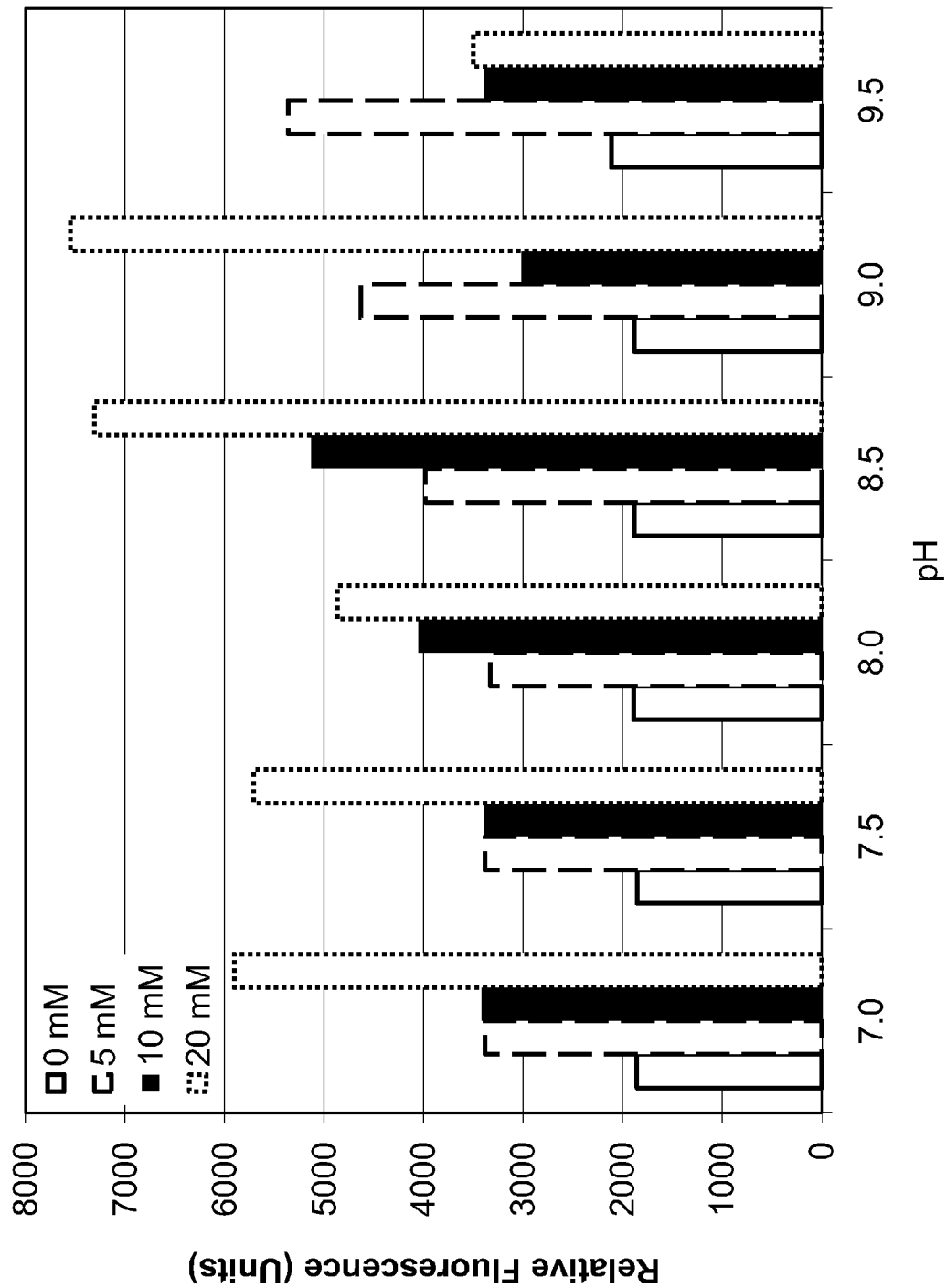
FIG. 9 is a graph showing the readthrough efficiency of another pyrrolysine analog of the present disclosure based on differences in concentration and pH.

The results are seen in FIG. 9. This analog (and similar analogs) can be used to prepare deubiquitinase inhibitors, with potentially higher specificity compared to other methods.

Example 15

A thymine-DNA glycosylase (TDG) protein was site-specifically SUMOylated.

First, a SUMO-SR complex was generated from SUMO-intein. SUMO-intein construct was expressed in BL21R2 cells by induction at 25° C. overnight with shaking at 225 rpm. Cells were pelleted at 8000 rpm for 5 minutes and the pellet was resuspended in 1×PBS (200 mM NaCl pH 8.0). Cells were sonicated at 50% power for 15 minutes total time and centrifuged at 10000 rpm for 10 minutes to recover the supernatant containing the protein. The supernatant lysate was bound to a His60 (Ni— affinity resin) column for 1 hour at 4° C. with gentle shaking. The column was washed with increasing concentrations of imidazole and SUMO-intein was eluted using 100-500 mM imidazole in PBS. Protein samples were mixed with 100 mM MESNa and incubated for 24 hours at room temperature with gentle shaking. Samples were then directly loaded onto chitin beads to bind the cleaved intein-CBD fragment to the beads and incubated with the beads at 4° C. for 1 hour. The flowthrough was collected and the resin was washed with 1 ml of PBS for 3×. Wash and flowthrough samples were bound to an Ni affinity column to purify the thioester form of SUMO from MESNa and other contaminants. The SUMO thioester was eluted off the His60 column at 100-200 mM imidazole concentrations and dialyzed into 50 mM HEPES pH 8.5+200 mM NaCl. Purified SUMO was verified using MALDI to bear the thioester form (MW of 12944 Da for NTHSUMO1-gly-CO—S—$CH_2CH_2SO_3^-$ versus 12819 Da for NTHSUMOl-gly-COOH) and stored in presence of 10 mM MESNa and 1 mM TCEP before being used for ligation.

Second, a loaded TDG-GST protein-enzyme complex was generated for ligation. The acronym "GST" refers to glutathione-5-transferase. The complex included a pyrrolysine analog of Formula (1). GST-tagged TDG protein was expressed in a Duet vector (bearing two expression cassettes) along with the pyrrolysine loading tRNA and aminoacyl synthetase in BL21R2 cells. Expression involved growing the cells initially up to A600=0.25, adding 2 mM of the pyrrolysine analog of Formula (I), growing cells to A600=0.5, and then adding another 3 mM PCA and 0.2 mM IPTG to induce the cells overnight at 25° C. Induced cells were lysed by sonication for 15 min (50% power, 10 sec on/off cycles) and then centrifuged at 10,000 rpm for 30 minutes. Supernatant was loaded on a glutathione column and incubated for 1 hour at 4° C., washed with 10× column volumes of 50 mM HEPES+500 mM NaCl pH 7.5. Bound proteins were eluted with 50 mM glutathione in the wash buffer. Eluted protein was dialyzed into 50 mM HEPES and 200 mM NaCl buffer pH 8.5 for use in ligation.

Third, a protein ligation reaction was performed. Purified TDG (0.85 mg) was added to thioester of SUMO (1.7 mg) in a mass ratio of 1:2. The sample was incubated at room temperature with gentle mixing. The sample had MESNa at a concentration of 7 mM MESNa during the reaction. Ligation samples were taken at 0 hour, 16 hour and 24 hour time points. Samples were run on SDS-PAGE gel to confirm ligation. The presence of ligated samples were detected by the following 3 methods: (1) Formation of a new high molecular weight band at 100 kDa on the gel; (2) Reactivity of the 100 kDa band against anti-SUMO and anti-TDG antibodies; and (3) protein ID of the Coomasie stained band of ligated product.

Example 16

A cyclic peptide was linked to mCherry. Cyclic peptides, being entropically constrained, can have higher binding characteristics.

Figure 10:
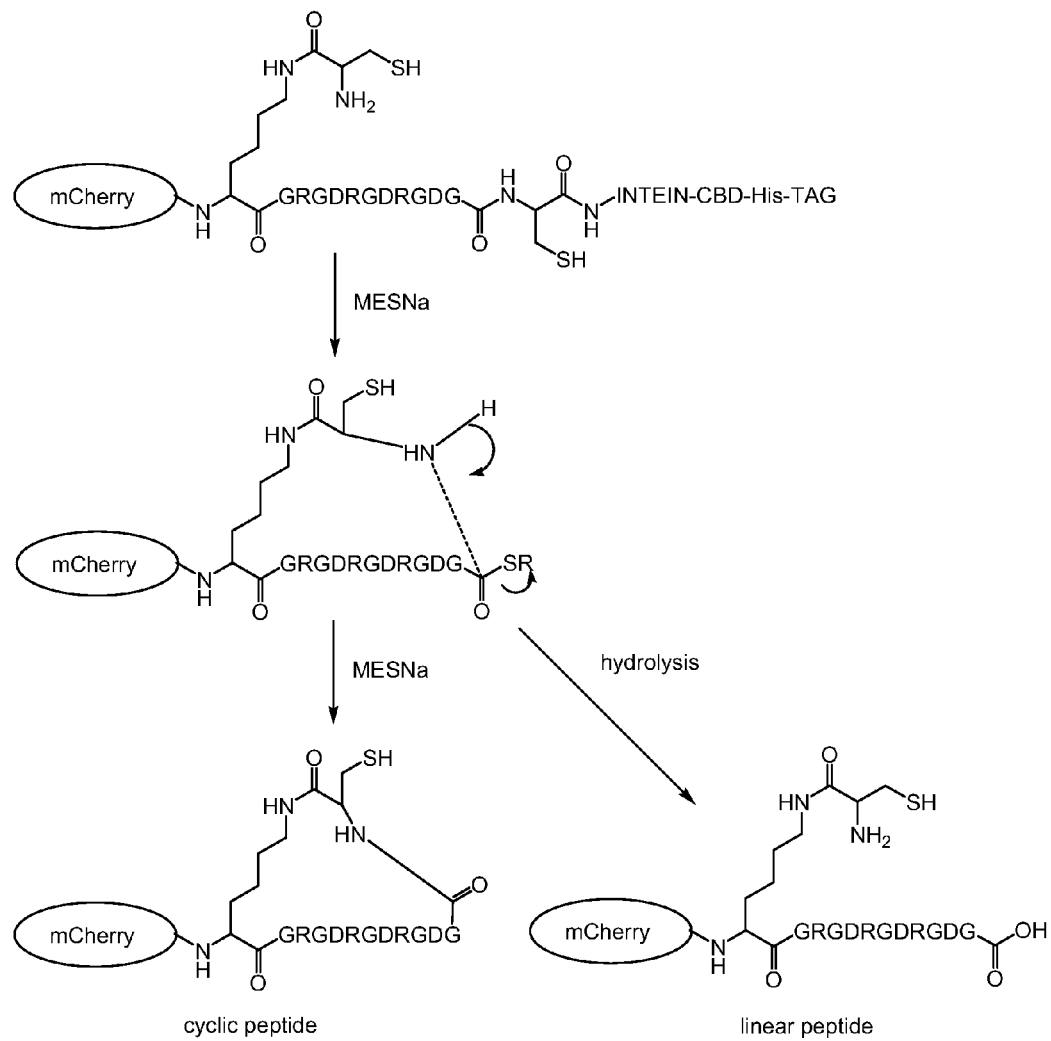
FIG. 10 is a general diagram showing the formation of a cyclic peptide using a pyrrolysine analog of the present disclosure.

The general scheme is shown in FIG. 10. The beginning mCherry-linked peptide contains a pyrrolysine analog of Formula (II) and a His-TAG which is used for purification. After purification, exposure to MESNa results in cleavage of the intein to obtain a protein with a thioester end. Exposure to MESNa also causes the thioester to react with the pyrrolysine analog, causing cyclization of the peptide. A trypsin cleavage site is present in the peptide for confirmation of cyclization during mass spectrometry. It is also possible that simple hydrolysis results in an uncyclized or linear peptide.

A plasmid was constructed with pyIST in the pETduet MCS1 and the sequence mCherry-stop codon-GRGDRGDRGDG-intein-CBD-hisTag (mCherryRGD3) in pETduet MCS2. The plasmid was transformed into BL21 (DE). mCherryRGD3 was overexpressed by the addition of 0.3 mM IPTG, 5 mM pyrrolysine analog, and 1M Tris-HCl pH 9.5 to adjust the pH of the cell culture to a slightly alkaline condition (~pH 8.0). The cells were grown at 25° C. overnight. mCherryRGD3 was purified using His-tag purification. mCherryRGD3 eluted at 75-200 mM imidazole. 100 mM MESNa was added to initiate intein cleavage and mCherryRGD3 cyclization. The reaction was wrapped in foil and incubated at room temperature for over 72 hours. The reaction mixture was then incubated with 1 mL chitin resin (New England BioLab) for 2 hours at 4° C. The supernatant from the chitin purification was concentrated and buffer exchanged into 100 mM HEPES, pH 8.0; 100 mM NaCl using Amicon MWCO 10 KDa. A sample was analyzed on SDS-PAGE to verify mCherryRGD3 expression. The resultant supernatant was also sent for mass spectrometry analysis by trypsin digestion. The cyclized peptide should have a modified pyrrolysine analog, while the linear peptide will not.

The mass spectrometry results indicated that the GDG end of the peptide reacted with the amino group on the end of the pyrrolysine analog. The ratio of linear peptide to cyclized peptide was about 0.27:1.

A gel-based assay was also used to monitor the cyclization of the peptide attached to mCherry. 50 mM fluorescein (FL) was prepared by dissolving the compound in DMSO. 300 μL of purified mCherryRGD3 was set aside for MESNa cleavage and RGD3 cyclization. Briefly, 100 mM MESNa was added to the 300 μL protein solution and at each time point indicated (0, 1, 2, 4, 8, 16, 24, 36, 48, 72-hr), 30 μL of the reaction was taken out.

To each 30 μL MESNa-cleaved reaction mixture, 0.6 μL [50 mM] FL was added and incubated at room temperature for 1 hour. 100 mM DTT was subsequently used to quench the reaction. The quenching was allowed to proceed for 1 hour at room temperature. 5×SDS loading dye was added to the quenched reaction, and the sample was boiled at 100° C. for 5 minutes, then frozen at −80° C. until all time points were taken.

Figure 11:
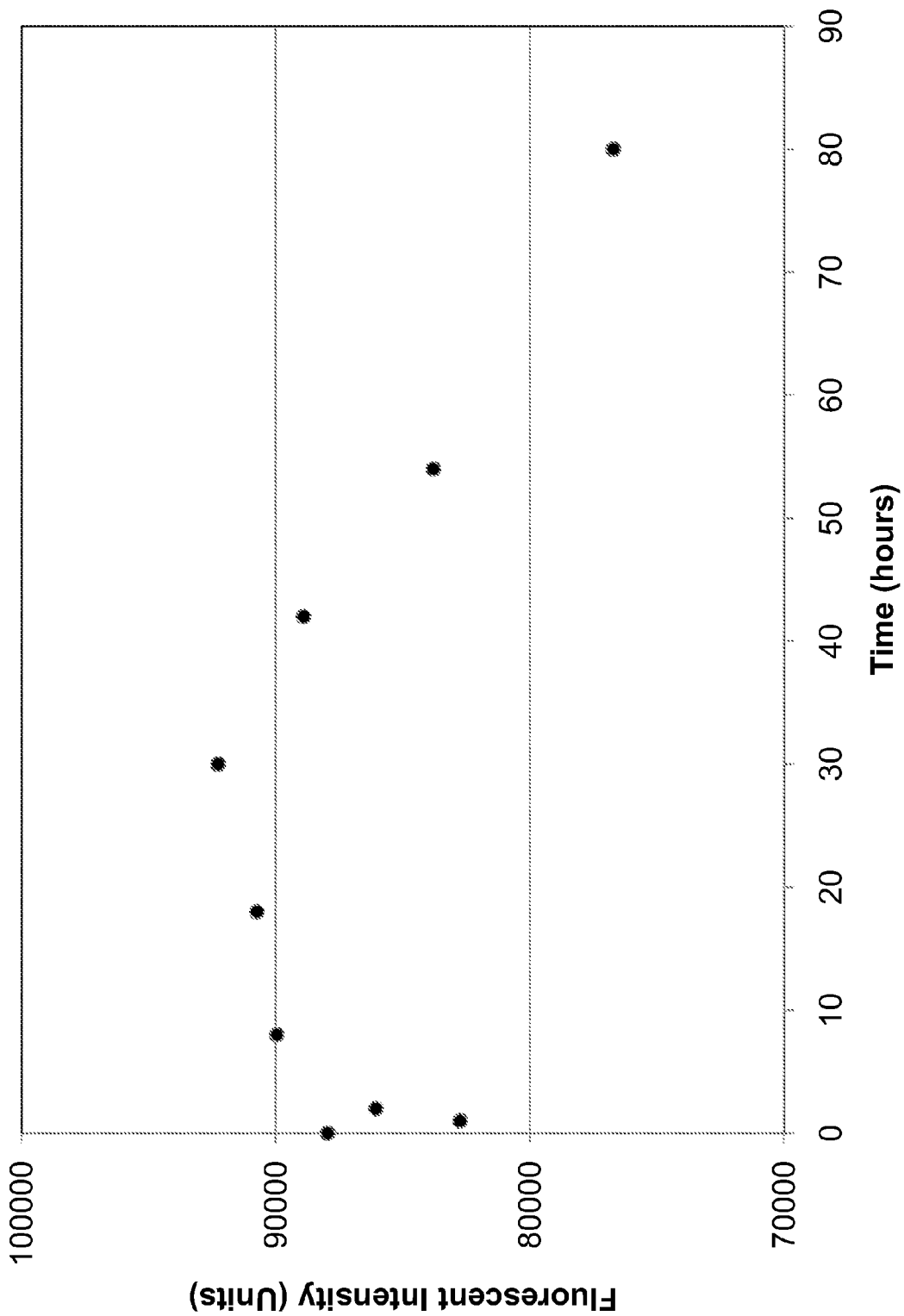
FIG. 11 is a graph showing a cyclization reaction through change in fluorescence.

Frozen samples for all time points were then thawed and run on a SDS-PAGE gel. The gel was scanned using a GE Typhoon scanner with the green laser and its corresponding filter set. The relative fluorescence intensity was quantified using ImageQuant software, and is shown in FIG. 11. This graph shows that the cyclization reactions take around 70-80 hours.

Example 17

The uptake of mCherry-cyclic(RGD)$_3$ protein into MCF-7 breast cancer cells was monitored by flow cytometry.

MCF-7 cells were cultured in Eagle's medium (Gibco) with 10% fetal bovine serum (FBS, Gibco), 0.01 mg/mL bovine insulin, 2 mM glutamine, 5 I.U. penicillin and 5 μg/mL streptomycin at 37° C./5% $CO_2$. Cells were plated at $5 \times 10^5$ density in a 48-well UPCELL plate (Thermo) and incubated at 37° C./5% $CO_2$ for 12 hours. Cells were washed with 1 mL PBS and then incubated with 2 μM wild-type mCherry in 500 μL plain Eagle's medium, 2 μM mCherry-oxo-RGD3 in 500 μL plain Eagle's medium, and 2 μM mCherry-PCA-RGD3 in 500 μL plain Eagle's medium, respectively for 4-hour and 8-hour. Sets of duplicates were set up for each condition and time point.

At the end of the incubation period, cells were washed 3 times with PBS. Cells were then incubated in 200 μL PBS at room temperature for 2 hours to allow the detachment of the cells from the plate. Flow cytometry was performed on an ICyte Reflection instrument at 25° C. Cells were analyzed using filters for mCherry emission to determine the amount of peptide taken up into the cells. $10^4$ cells were analyzed for each sample.

The results are shown in Table 1 below.

TABLE 1

|  | Uptake (%) |
| --- | --- |
| negative Control | 0.28 |
| mCherry Control | 0.71 |
| linear mCherry-(oxo)(RGD)$_3$ | 2.82 |
| Cyclic mCherry-(PCA)-(RGD)$_3$ | 6.04 |

As expected, the cyclized mCherry-(PCA)-(RGD)$_3$ protein was uptaken by MCF-7 cells much better than the mCherry control and twice as well as linear mCherry-(oxo)(RGD)$_3$ protein.

One advantage of cyclic peptides generated using pyrrolysine analogs is that they are stable in the cell. Thus they can be used to inhibit intracellular targets.

Example 18

The pyrrolysine analog of Formula (17), having a terminal azide group, was prepared as shown below:

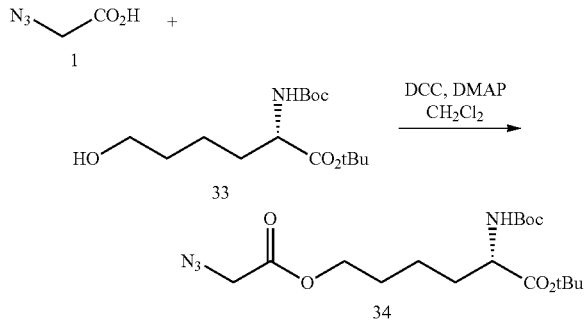

t-Butyl 2-azidoacetyloxy-(S)-2-(tert-butoxycarbonylamino)hexanoate (34)

To a solution containing acid 1 (96 mg, 0.95 mmol), alcohol 33 (303 mg, 1.0 mmol), and 4-(dimethylamino)pyridine (DMAP, 12 mg, 0.1 mmol) in $CH_2Cl_2$ (5 mL) was added a solution of N,N'-dicyclohexylcarbodiimide (DCC, 206 mg, 1.0 mmol) in $CH_2Cl_2$ (5 mL) dropwise over 15 minutes. The resulting suspension was stirred at room temperature for 20 hours, evaporated in vacuo, re-suspended in EtOAc (5 mL), and passed through a plug of CELITE. The filtrate was evaporated in vacuo to give a yellow oil that was purified by flash chromatography (silica gel; hexanes→hexanes/EtOAc, 4/1) providing the title compound 34 (337 mg, 92%) as a clear oil.

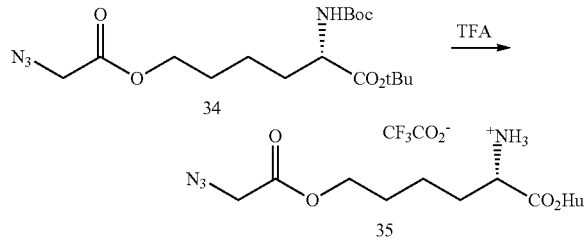

(S)-2-Amino-6-azidoacetyloxyhexanoic acid trifluoroacetate (35)

A solution of the protected lysine derivative 34 (320 mg, 0.83 mmol) in TFA (5 mL) was stirred at room temperature for 2 hours and then evaporated in vacuo. The residue was co-evaporated four times with MeOH (4×5 mL) and once with $CH_2Cl_2$ (5 mL) to give the title compound 35 (290 mg, ~100%) as a clear oil.

Example 19

The pyrrolysine analog of Formula (19) was prepared as shown below:

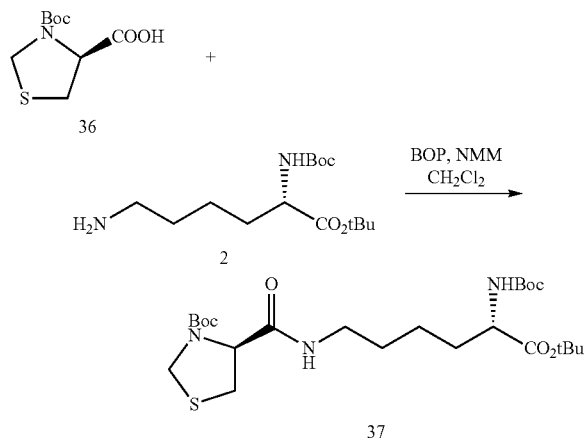

tert-Butyl $N^2$-tert-butoxycarbonyl-$N^6$-((S)-3-(tert-butoxycarbonyl) thiazolidine-4-carbonyl)lysinate (37)

To a solution of acid 36 (8.30 g, 35.6 mmol) and Boc-Lys-OtBu (2, 10.8 g, 35.6 mmol) in $CH_2Cl_2$ (250 mL) was added N-methylmorpholine (NMM, 8.6 mL, 78 mmol) followed by benzotriazol-1-yloxy)tris(dimethylamino)phosphonium hexafluorophosphate (BOP, 17.3 g, 39.2 mmol). The reaction mixture was stirred at room temperature for 19 hours and then diluted with brine (100 mL). The phases were separated and the extraction was completed with additional portions of $CH_2Cl_2$. The combined extracts were dried ($MgSO_4$), and evaporated in vacuo to give a yellow oil. Purification by flash chromatography (silica gel; hexanes→hexanes/EtOAc, 1/1) gave the title compound 37 (17.2 g, 94%) as a clear oil.

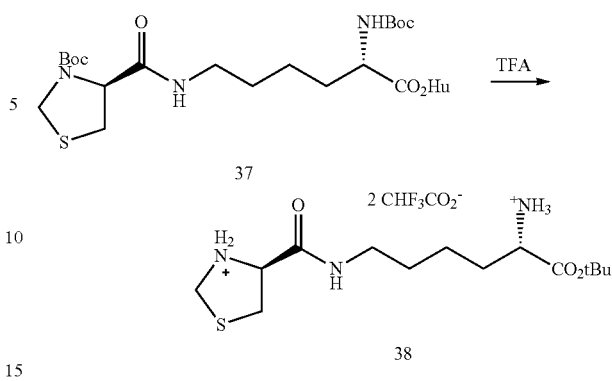

$N^6$-((S)-Thiazolidine-4-carbonyl)lysine ditrifluoroacetate (38)

A solution of the lysine derivative 37 (17.2 g, 33.3 mmol) in TFA (200 mL) was stirred at room temperature for 2 hours and evaporated in vacuo. The residue was co-evaporated four times with MeOH (4×30 mL) and triturated with $Et_2O$ (200 mL). The resulting suspension was decanted, and the precipitate dried in vacuo to give the title compound 38 (16.5 g, ~100%) as a white powder.

Example 20

Figure 13:
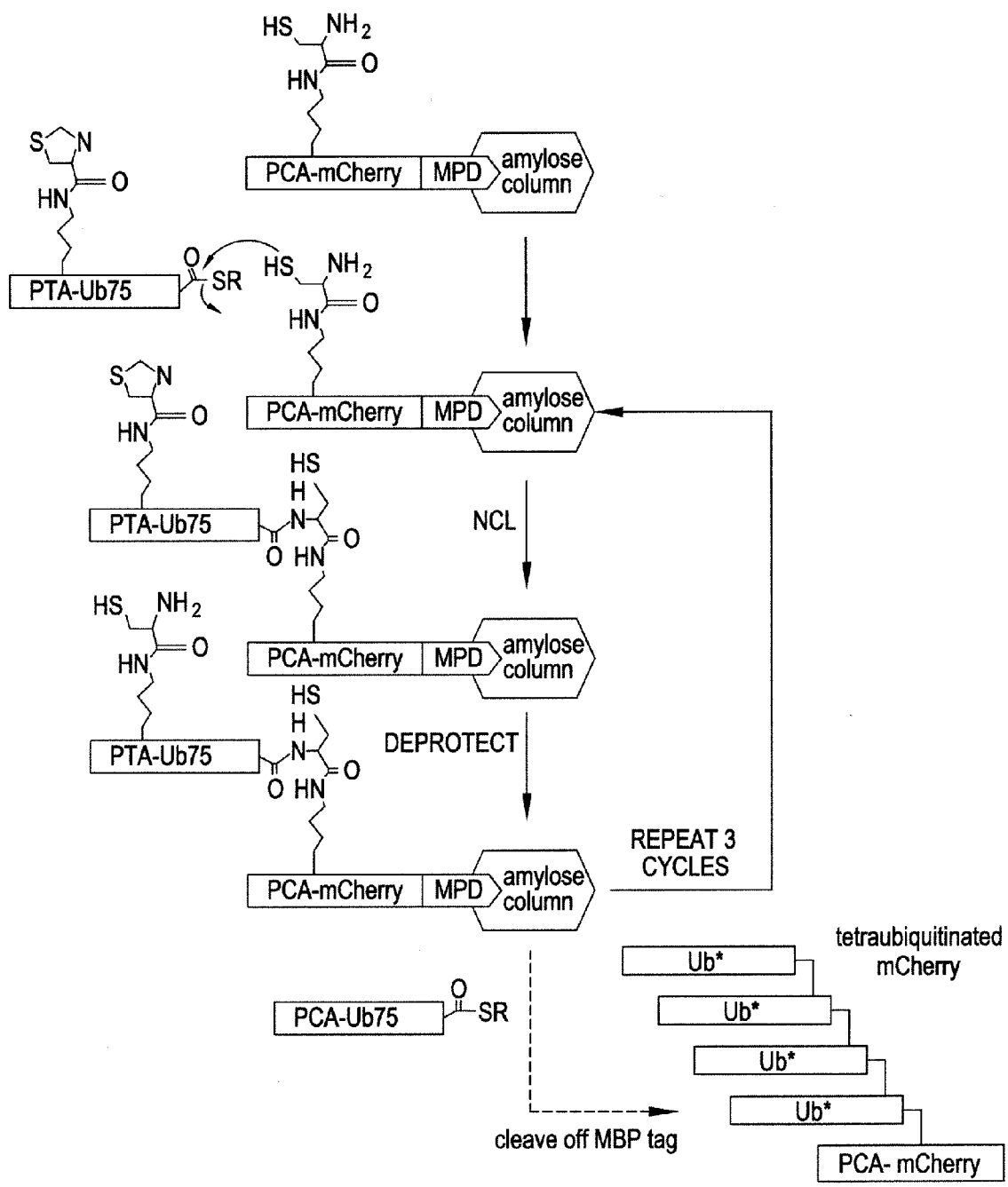
FIG. 13 is a diagram illustrating the sequential synthesis of a polyubiquitinated protein.

The pyrrolysine analogs of Formulas (18) and (19) can be considered protected forms of the pyrrolysine analogs of Formula (I). They can be used for sequential couplings of ubiquitinated subunits by iterative native chemical ligation/deprotection steps, as illustrated in FIG. 13. Here, a PCA-mCherry protein has been modified to incorporate a pyrrolysine analog of Formula (I). The PCA-mCherry protein is attached to a column. A ubiquitin protein has been modified to incorporate a pyrrolysine analog of Formula (XIX) (labeled here as PTA-Ub75). The C-terminal thioester on the PTA-Ub75 reacts with the pyrrolysine analog of the PCA-mCherry protein (via native chemical ligation, or NCL) to ubiquitinate the PCA-mCherry protein. The thiazolidine group on the PTA-Ub75 can then be deprotected, for example with hydroxylamine or other standard methods, to provide new amine and thiol groups which can subsequently reacted with the C-terminal thioeseter on another PTA-Ub75. This reaction can continue sequentially to obtain a PCA-mCherry protein that is tetraubiquitinated at the same location. A key difference by comparison with previous routes is that the proximal ubiquitin is anchored to the column, not the distal ubiquitin. It should be sufficient to prepare just seven tagged Ub75 thioesters and one non-tagged Ub75 thioester precursor to be able to generate any monoubiquitinated, multiubiquitinated, or polyubiquitinated protein via this method.

Figure 14:
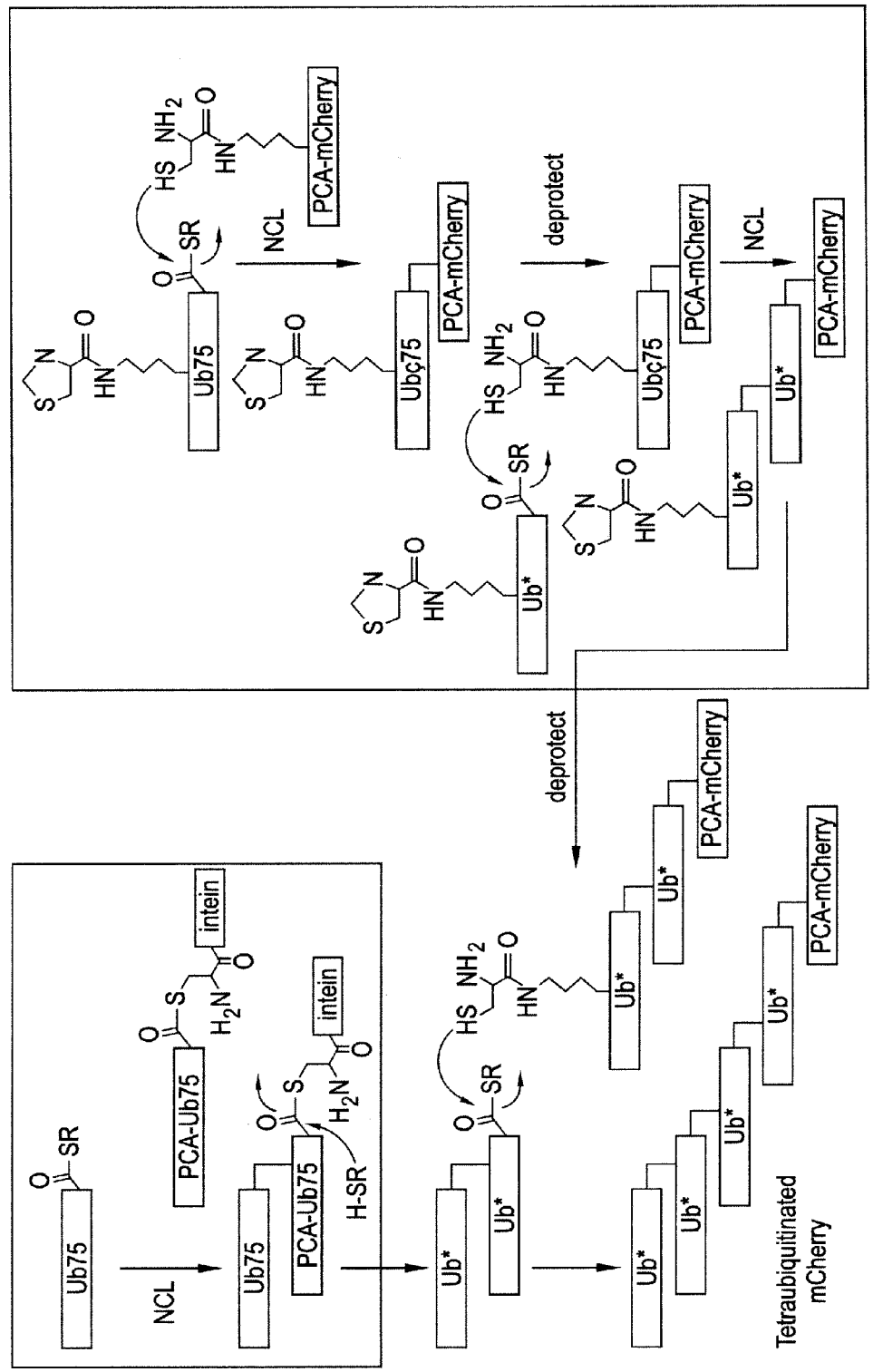
FIG. 14 is a diagram illustrating the convergent synthesis of a polyubiquitinated protein.

Another alternative for generating a tetraubiquitinated PCA-mCherry protein is through convergent synthesis as shown in FIG. 14. As shown in the right-hand side, a PCA-mCherry protein incorporates a pyrrolysine analog of Formula (I). A ubiquitin protein has been modified to incorporate a pyrrolysine analog of Formula (XIX) (labeled here as Ub75). The C-terminal thioester on the Ub75 reacts with the pyrrolysine analog of the PCA-mCherry protein to ubiquitinate the PCA-mCherry protein. The thiazolidine group is then deprotected (labeled here as Ubç75). The Ubç75 is then reacted with a second ubiquitin unit (labeled Ub*) containing a pyrrolysine analog of Formula (XIX). This thiazolidine unit is then deprotected as well.

On the left-hand side of FIG. 14, another ubiquitin unit, labeled as PCA-Ub75, is attached to an intein. The PCA-Ub75 protein has incorporated a pyrrolysine analog of Formula (I) as well. A ubiquitin unit is attached to the pyrrolysine analog, and the intein is then cleaved. This diubiquitinated subunit is then reacted with the diubiquitinated subunit from the right-hand side to obtain the tetraubiquitinated mCherry protein.

Polyubiquitinated proteins are targets for protein degradation. One appeal of using a tetraubiquitinated mCherry protein is that this protein potentially provides a facile fluorescence-based assay for monitoring its own degradation, with the time dependence of the fluorescence decrease providing a measurement of the rate of the degradation.

The readthrough efficiencies of the two analogs of Formulas (18) and (19), containing a thiazolidine moiety, were determined by using mCherry assay.

A plasmid containing the mCherry coding sequence was obtained. The AAG codon of Lys55 was replaced with TAG using the Stratagene QuikChange® site-directed mutagenesis kit. The resulting mutant (Lys55Pyl) was then inserted between the NdeI and KpnI restriction sites into a pETDuet-derived pPylST harboring the pylS and pylT genes4 to generate the plasmid pPylST_mCherry(Lys55Pyl). The sequence of the mCherry(Lys55Pyl) insert was confirmed by DNA sequencing. The pPylST_mCherry(Lys55Pyl) was then transformed into E. coli strain BL21(DE3) and a single colonized transformant was inoculated into 3 mL of the Luria-Bertani (LB) medium supplemented with 50 mg/mL of ampicillin and incubated overnight at 37° C. while shaking. 0.6 mL of this starter culture was subsequently inoculated into 50 mL of the Terrific Broth medium and grown at 37° C. with shaking at 250 rpm. The expression of the mutated mCherry was induced by adding 25 mM TrisCl (pH 9.0) and 0.3 mM IPTG (isopropyl β-D-1-thiogalactopyranoside) after the $OD_{600}$ had reached 1.0.

To determine the incorporation efficiency, each analog was mixed individually with 500 µL of the induction culture media in a sterile 24-well tissue culture plate. Each analog was tested at four different concentrations: 1 mM, 2.5 mM, 5 mM, and 10 mM. As a control, the same volume of the induced culture was used without addition of the analog. The plate was subsequently incubated at 28° C. while shaking at 180 rpm for 16 hours and then scanned on a Typhoon fluorescence scanner with a 532-nm excitation laser and a 670-nm emission filter. The fluorescence intensity of each well was integrated by using ImageQuant software and normalized by subtracting the intensity of the control. The experiment was run independently three times and the mean values and standard deviations were calculated.

Figure 12:
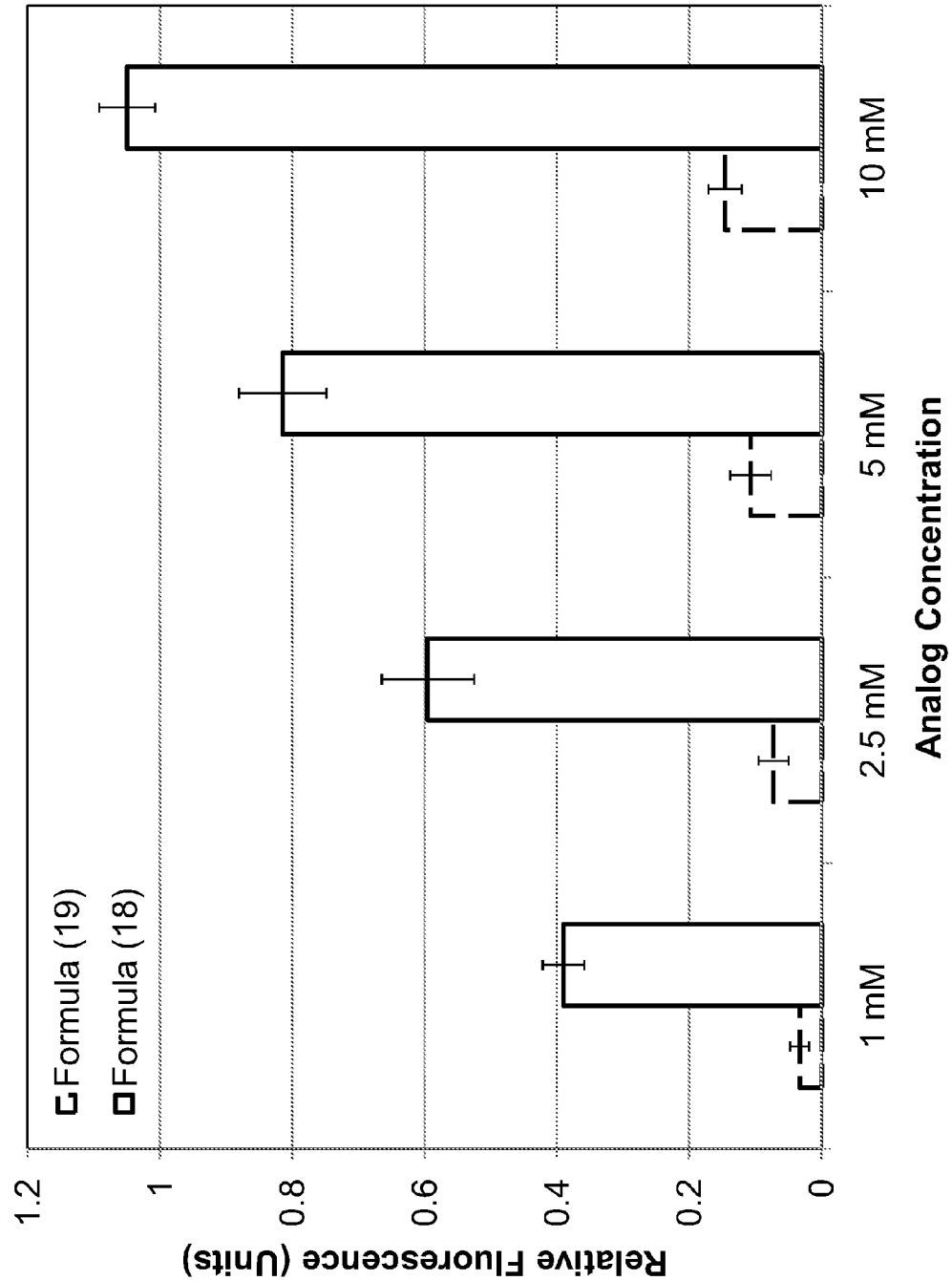
FIG. 12 is a graph comparing the readthrough efficiency of two stereoisomers of a pyrrolysine analog of the present disclosure as a function of concentration.

FIG. 12 is a graph showing the results. It can be seen that the analog of Formula (18) was incorporated significantly more successfully than that of Formula (19) at all concentrations.

Example 21

Figure 15:
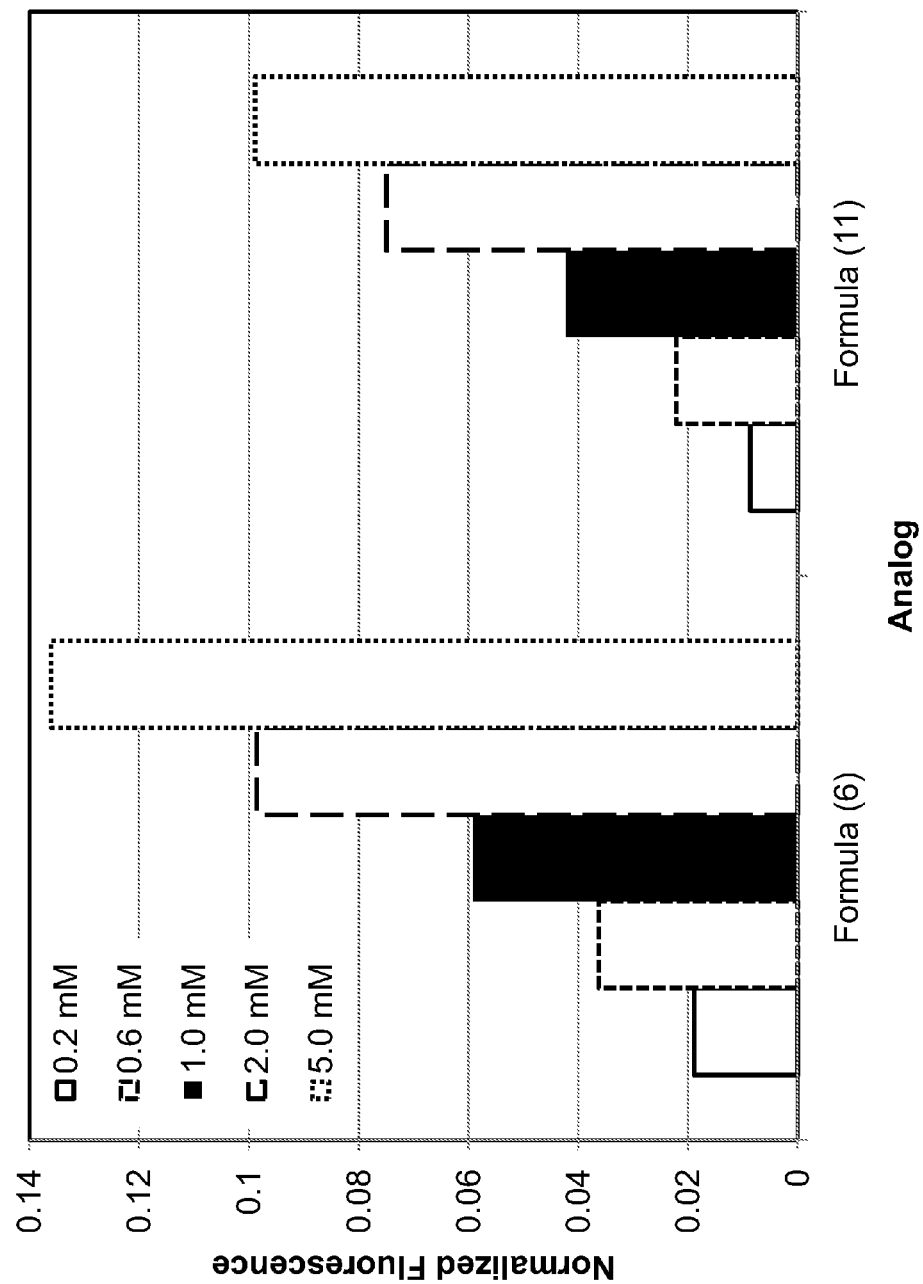
FIG. 15 is graph showing the readthrough efficiency of two pyrrolysine analogs of the present disclosure based on differences in concentration.

The relative readthrough efficiency of the pyrrolysine analog of Formula (11), containing a diazirine moiety, was compared to that of the pyrrolysine analog of Formula (6), at five different analog concentrations: 0.2 mM, 0.6 mM, 1.0 mM, 2.0 mM, and 5.0 mM. The results are shown in FIG. 15. The values here are normalized against the fluorescence obtained when measuring the readthrough efficiency of the analog of formula (C1) in Example 2 at a concentration of 2.0 mM. As seen here, the analog of Formula (11) performed well, even though it did not perform as efficiently as Formula (6).

The compositions, processes, and applications of the present disclosure have been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A pyrrolysine analog of Formula (I):

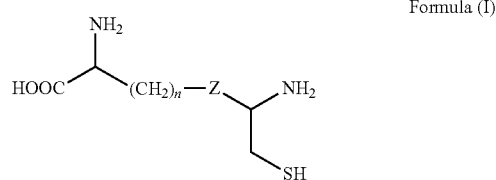

Formula (I)

wherein n is from 0 to 8; and Z is a linkage selected from the group consisting of ester, thioester, carbonyl, ether, thioether, carbamate, and amide.

2. The analog of claim 1, wherein Z is amide, ester, or carbonyl.

3. The pyrrolysine analog of claim 1, wherein the analog has the structure of Formula (II):

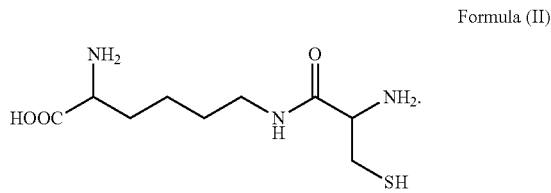 [SMILES: NC(CCCCNC(=O)C(N)CS)C(=O)O]

Formula (II)

4. The pyrrolysine analog of claim 3, wherein the analog has the structure of Formula (1):

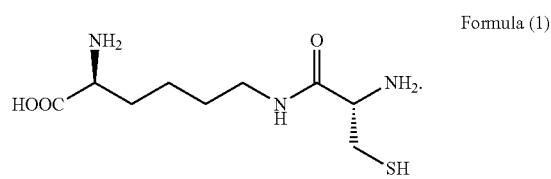 [SMILES: N[C@H](CS)C(=O)NCCCC[C@H](N)C(=O)O]

Formula (1)

5. The pyrrolysine analog of claim 3, wherein the analog has the structure of Formula (2):

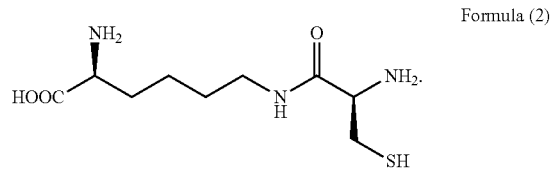 [SMILES: N[C@@H](CCCCNC(=O)[C@@H](N)CS)C(=O)O]

Formula (2)

6. The pyrrolysine analog of claim 1, wherein the analog has the structure of Formula (16):

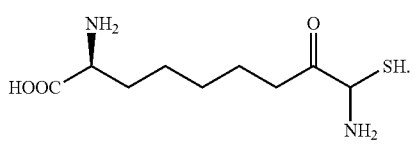

Formula (16)

7. A pyrrolysine analog of Formula (XI):

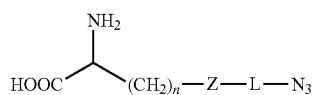

Formula (XI)

wherein n is from 0 to 8;

Z is a linkage selected from the group consisting of ester and amide; and

L is a linkage selected from the group consisting of alkyl and cycloalkyl, either of which may be substituted with one or more substituents selected from the group consisting of alkoxy, halogen, hydroxyl, amino, and thiol.

8. The analog of claim 7, wherein L is alkyl or substituted alkyl.

9. The analog of claim 7, wherein L has an amino substituent.

10. A pyrrolysine analog of Formula (IV) or Formula (V):

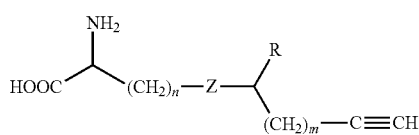

Formula (IV)

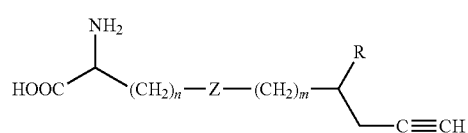

Formula (V)

wherein m is from 1 to 6; and

R is selected from the group consisting of alkoxy, halogen, hydroxyl, amino, and thiol.

11. The analog of claim 10, wherein the analog has the structure of Formula (4), (5), or (6):

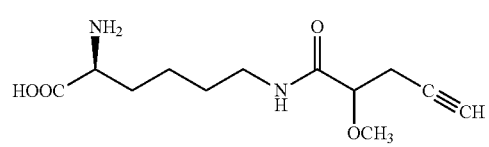

Formula (4)

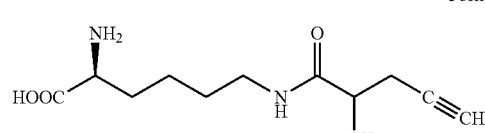

Formula (5)

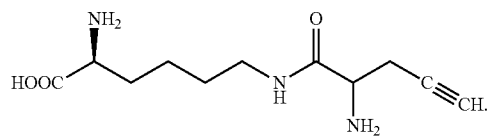

Formula (6)

12. The analog of claim 10, wherein the analog has the structure of Formula (15):

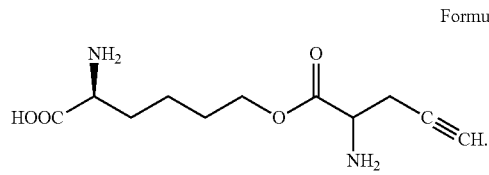

Formula (15)

13. The analog of claim 7, wherein the analog has the structure of Formula (10):

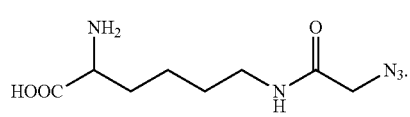

Formula (10)

14. The analog of claim 7, wherein the analog has the structure of Formula (17):

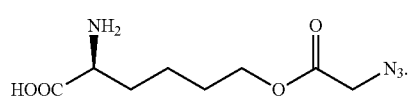

Formula (17)

15. A pyrrolysine analog of Formula (XII) or Formula (XVIII):

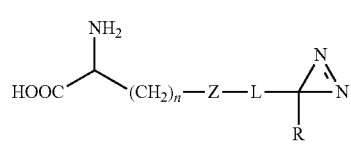

Formula (XII)

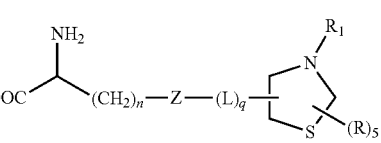

Formula (XVIII)

wherein n is from 0 to 8;

Z is a linkage selected from the group consisting of ester, thioester, carbonyl, ether, thioether, and amide;

L is a linkage selected from the group consisting of alkyl, cycloalkyl, and heterocyclic, any of which may substituted with one or more substituents selected from the group consisting of alkoxy, halogen, hydroxyl, amino, and thiol;

q is 0 or 1; and

R₁ and each R are independently selected from the group consisting of hydrogen, alkyl, alkoxy, halogen, hydroxyl, amino, and thiol.

16. The analog of claim 15, wherein the analog has the structure of Formula (11):

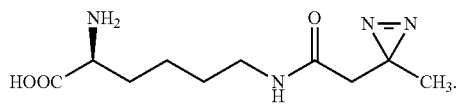

Formula (11)

17. The analog of claim 15, wherein the analog has the structure of Formula (12):

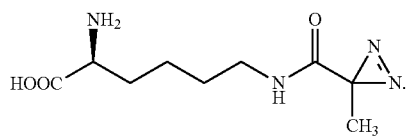

Formula (12)

18. The analog of claim 15, wherein the analog has the structure of Formula (18) or (19):

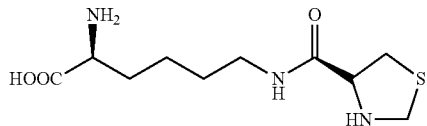

Formula (18)

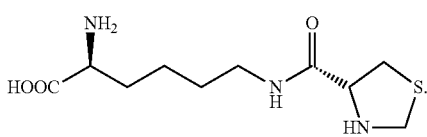

Formula (19)

19. The analog of claim 15, wherein the analog has the structure of Formula (14):

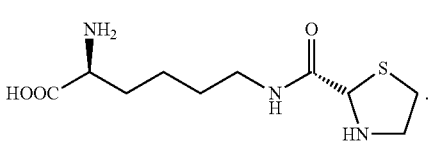

Formula (14)

* * * * *